(12) United States Patent
Hoeijmakers et al.

(10) Patent No.: US 7,820,374 B2
(45) Date of Patent: Oct. 26, 2010

(54) DETECTION METHODS BASED ON HR23 PROTEIN BINDING MOLECULES

(75) Inventors: Jan H. J. Hoeijmakers, Zevenhuizen (NL); Steven Berglink, Rotterdam (NL); Gijsbertus Theodoras Johannes van der Horst, Rhoon (NL); Wim Vermeulen, Zwijndrecht (NL); Mei Yin Ng, Philadelphia, PA (US)

(73) Assignee: Erasmus Universiteit Rotterdam, Rotterdan (NL)

( * ) Notice: Subject to any disclaimer, the term of this patent is extended or adjusted under 35 U.S.C. 154(b) by 1207 days.

(21) Appl. No.: 10/301,498

(22) Filed: Nov. 20, 2002

(65) Prior Publication Data

US 2003/0124605 A1 Jul. 3, 2003

Related U.S. Application Data

(60) Provisional application No. 60/331,773, filed on Nov. 21, 2001.

(51) Int. Cl.
*C12Q 1/68* (2006.01)
*C12Q 1/66* (2006.01)
*G01N 33/53* (2006.01)

(52) U.S. Cl. .............................. 435/6; 435/7.1; 435/8; 435/29

(58) Field of Classification Search ........................ None
See application file for complete search history.

(56) References Cited

OTHER PUBLICATIONS

Volker et al. Sequential assembly of the nucleotide excision repair factors in vivo. Molecular Cell. vol. 8, pp. 213-224, Jul. 2001.*
Fitch et al. p53 responsive nucleotide excision repair gene products p48 and XPC, but not p53, localize to sites of UV-irradiation-induced DNA damage, in vivo. Carcinogenesis, vol. 24, pp. 843-850, May 2003.*
Kroese et al. Genetic tests and their evaluation: can we answer the key questions? Genetics in Medicine, vol. 6, pp. 475-480, 2004.*
"analogue." Merriam-Webster Online Dictionary. 2008. Merriam-Webster Online. May 22, 2008 ,http://www.merriam-webster.com/dictionary/analogue>.*
"irradiate." Merriam-Webster Online Dictionary. 2008. Merriam-Webster Online. May 22, 2008 <http://www.merriam-webster.com/dictionary/irradiate>.*
Hoogstraten et al. Versatile DNA damage detection by the global genome nucleotide excision repair protein XPC. Journal of Cell Science, vol. 121, pp. 2850-2859, 2008.*

Uchida et al. The carboxy-terminal domain of the XPC protein plays a crucial role in nucleotide excision repair through interactions with transcription factor IIH. DNA Repair, vol. 1, No. 6, pp. 449-461, Jun. 2002.*
Masutani et al. Identification and characterization of XPC-binding domain of hHR23B. Molecular and Cellular Biology, vol. 17, No. 12, pp. 6915-6923, Dec. 1997.*
Yamaizumi et al., U.v.-induced nuclear accumulation of p53 is evoked through DNA damage of actively transcribed genes independent of the cell cycle, Oncogene, 1994, pp. 2775-2784, vol. 9, No. 10.
Batty et al., Stable Binding of Human XPC Complex to Irradiated DNA Confers Strong Discrimination for Damages Sites, Journal of Molecular Biology, 2000, pp. 275-290, vol. 300, No. 2.
Hey et al., the XPC-HR23B Complex Displays High Affinity and Specificity for Damaged DNA in a True-Equilibrium Fluorescence Assay, Biochemistry, May 28, 2002, pp. 6583-6587, vol. 41, No. 21.
Sugasawa et al., Xeroderma Pigmentosum Group C Protein Complex Is the Initiator of Global Genome Nucleotide Excision Repair, Molecular Cell, Aug. 1998, pp. 223-232, vol. 2, No. 2.
Yokoi et al., The Xeroderma Pigmentosum Group C Protein Complex XPC-HR23B Plays an Important Role in the Recruitment of Transcription Factor IIH to Damaged DNA, Mar. 2000, pp. 9870-9875, vol. 275, No. 13.
Ng et al., Developmental Defects and Male Sterility in Mice Lacking the Ubiquitin-Like DNA Repair Gene mHR23B, Molecular and Cellular Biology, Feb. 2002, pp. 1233-1245, vol. 22, No. 4.
Santagati et al., Different dynamics in nuclear entry of subunits of the repair/transcription factor TFIIH, Nucleic Acids Research, Apr. 1, 2001, pp. 1574-1581, vol. 29, No. 7.
PCT International Search Report, PCT/NL03/00812, Aug. 17, 2004.

* cited by examiner

*Primary Examiner*—Jennifer Dunston
(74) *Attorney, Agent, or Firm*—TraskBritt

(57) ABSTRACT

A method is provided for determining whether an agent is capable of inducing a DNA lesion in a eukaryotic cell, including exposing the eukaryotic cell to the agent and determining whether an HR23 protein-binding molecule accumulates in the cell, where the HR23 protein-binding molecule is preferably xeroderma pigmentosum group C (XPC), 3-methyladenine DNA glycosylase (MAG), CREB, p53, or a functional part, derivative, and/or analogue thereof. Preferably the cell overexpresses HR23A and/or HR23B protein. A rapid and sensitive test is provided with significant advantages over the Ames test. A method is provided for determining whether an agent is capable of inhibiting a cellular process, the process resulting in accumulation of HR23 protein-binding molecule within a cell. A method for determining whether a cell has an impaired DNA repair system is provided. An impaired DNA repair system is indicative for diseases such as xeroderma pigmentosum, cockayne syndrome, and/or trichothiodystrophy.

12 Claims, 9 Drawing Sheets

DETECTION METHODS BASED ON HR23 PROTEIN BINDING MOLECULES

CROSS-REFERENCE TO RELATED APPLICATIONS

This application claims priority under 35 U.S.C. §119(e) to U.S. Provisional Patent Application 60/331,773, filed on Nov. 21, 2001, the contents of the entirety of which are incorporated by this reference.

TECHNICAL FIELD

The invention relates generally to biotechnology, more particularly to the field of molecular biology.

BACKGROUND

The integrity of a cellular organism is continuously challenged during its lifetime. Internal and external factors, such as toxic compounds and radiation, are a threat to the wellbeing of such organism. Potentially harmful factors comprise factors capable of distorting cellular processes such as the generation of vital biomolecules and/or degradation of such molecules, notably nucleic acids and proteins. For instance, inhibitors of RNA or protein synthesis, transport or turn-over compromise cellular function. Additionally, many internal and external factors are capable of damaging cellular components, such as DNA.

Preservation of an intact genome is of utmost importance to living cellular organisms. However, the integrity of nucleic acids such as DNA is continuously challenged. Cells must overcome endogenous (for instance, metabolic) and exogenous (environmental) threats, as well as the intrinsic instability of chemical bonds in nucleic acid such as DNA itself (e.g., deamination and depurination). For instance, oxidative stress, ultraviolet (UV) light, ionizing radiation (such as X-rays), and numerous chemicals are capable of inducing a wide variety of lesions in DNA. An agent capable of inducing a DNA lesion is called a mutagen. A DNA lesion is defined herein as an alteration of DNA which involves a change in DNA sequence and/or a change in DNA structure. A DNA lesion can, for instance, comprise a DNA (double) strand break and/or an insertion/deletion of at least one nucleotide.

A DNA lesion can affect cellular processes and can have severe consequences for the wellbeing of an organism. Direct effects of DNA lesions at the cellular level comprise inhibition of vital processes like transcription and replication, triggering cell cycle arrest. Accumulation of lesions in DNA above certain thresholds can lead to permanent alterations in the genetic code, replicative senescence and/or to (programmed) cell death. Permanent alterations in the genetic code can, for instance, cause changes in metabolic processes, inborn defects and/or overall functional decline contributing to (premature) aging. Mutations, specifically in proto-oncogenes and tumor suppressor genes, are responsible for tumor initiation and subsequent progression of the multistep process of carcinogenesis. Replicative senescence and cell death can enhance the process of aging.

Potential mutagens are often tested with the widely used Ames test. This test is based upon reversion of mutations in a histidine (his) operon in the bacterium *Salmonella typhimurium*. The his operon encodes enzymes required for the biosynthesis of the amino acid histidine. Strains with mutations in the his operon are histidine auxotrophs: they are unable to grow without added histidine. Revertants that restore the his$^+$ phenotype will grow on minimal medium plates without histidine.

In the Ames test, the his$^-$ mutants are mixed with a potential mutagen and then plated on minimal medium with a very small amount of histidine. The concentration of histidine used is limiting, so after the cells go through several cell divisions, the histidine is used up and the auxotrophs stop growing. However, if the potential mutagen induces his$^+$ revertants during the initial few cell divisions, then each of the resulting revertants will continue to divide and form a colony. The number of colonies produced is proportional to how efficiently a mutagen reverts the original his$^-$ mutation.

A disadvantage of the Ames test is that it is unable to detect mutagenic agents that are activated by the eukaryotic (organ or tissue-specific) cellular metabolism (such as the class of p450 enzymes). Although preincubation of the agent to be tested with cellular extracts may partly overcome this limitation, the assay is still unreliable as it utilizes a bacterium to predict effects in a very different organism, such as a mammal, and/or in specific organs or tissues. Next to entire classes of false negative outcomes, also a significant number of false positive results have been obtained with the heterologous procaryotic system. Moreover, the test detects only mutagenic compounds but does not detect agents that have mainly a cytotoxic effect or induce deletions, or other chromosomal aberrations. Finally, the Ames test takes overnight incubation until the result is obtained. This is due to the fact that bacterial growth needs to be awaited.

DISCLOSURE OF THE INVENTION

The invention provides a novel test for detecting cells with DNA lesions. The invention also provides a novel test for detecting agents that are harmful to eukaryotic organisms. More specifically, the present invention provides a novel test for detecting agents that are mutagenic and/or cytotoxic for eukaryotic cells and a novel test for detecting agents capable of at least in part inhibiting proteolysis. The invention further provides a method for determining whether a cell has an impaired DNA damage repair mechanism.

The invention provides a method for detecting a DNA lesion in a eukaryotic cell, comprising determining whether an HR23 protein-binding molecule accumulates within the cell. The invention furthermore provides a method for determining whether an agent is capable of inducing a DNA lesion in a eukaryotic cell, comprising:

exposing at least one eukaryotic cell to the agent; and determining whether an HR23 protein-binding molecule accumulates within the cell.

Preferably, it is determined whether the HR23 protein-binding molecule accumulates in the nucleus of the cell.

By a "HR23 protein-binding molecule" is meant herein a molecule, for instance a peptide or protein, capable of specifically binding an HR23 protein. The HR23 protein-binding molecule may be a natural ligand of HR23. Alternatively, the HR23 protein-binding molecule may be an artificial binding partner of HR23.

Figure 1:
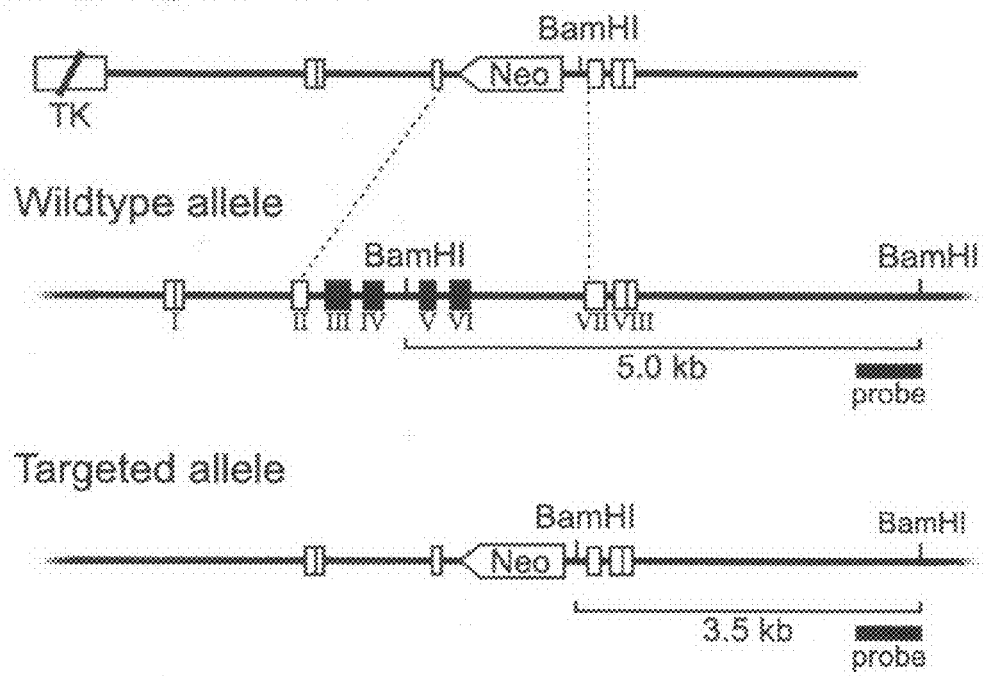
FIGS. 1A-1E. Targeted disruption of the mHR23A gene by homologous recombination.
Figure 1:
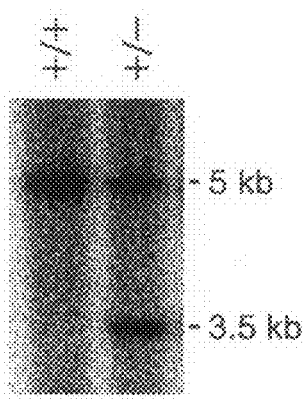
Figure 1:
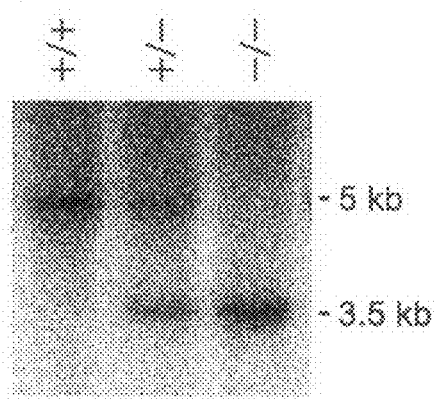
Figure 1:
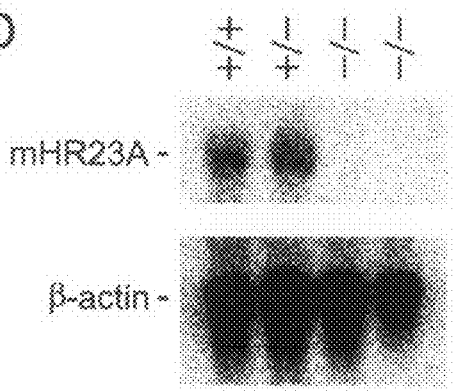
Figure 1:
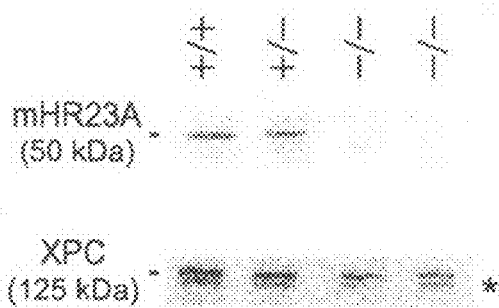

FIG. (1A) Genomic organization and disruption strategy for mHR23A depicting the gene, the targeting construct, and the targeted mHR23A allele. Exons III-VI (and part of exons II and VII) were replaced by the dominant selectable neomycin resistance marker transcribed in antisense orientation.

FIG. (1B) Southern blot analysis of BamHI-digested DNA from ES cells showing the 5.0 kb and 3.5 kb fragment representing the wild-type and the targeted allele of mHR23A, respectively.

FIG. (1C) Southern blot analysis of BamHI-digested tail DNA from mHR23A$^{+/+}$, mHR23A$^{+/-}$, and mHR23A$^{-/-}$ mice.

FIG. (1D) RNA blot analysis of mHR23A mRNA from mHR23A$^{+/+}$, mHR23A$^{+/-}$, and mHR23A$^{-/-}$ MEFs using mHR23A cDNA as a probe (upper panel). As a loading control for the amount of RNA, the blot was reprobed with β-actin cDNA (lower panel).

FIG. (1E) Immunoblot analysis of mHR23A protein in cellular extracts from mHR23A$^{+/+}$, mHR23A$^{+/-}$, and mHR23A$^{-/-}$ MEFs loaded in equal amounts. Polyclonal antibodies against the human HR23A protein (upper panel) and the human XPC protein (lower panel) were utilized. The asterisk indicates an aspecific cross-reacting band.

FIGS. 2A-2F. Repair characteristics of mHR23A$^{-/-}$ E13.5 and DKO E8.5 MEFs.

FIG. (2A) UV survival curves of primary mHR23A$^{+/+}$, mHR23A$^{+/-}$, and mHR23A$^{-/-}$ E13.5 MEFs. XPC$^{-/-}$ fibroblasts were included as a negative control. Cells were exposed to different doses of UV (254 nm). After 4-5 days, the number of proliferating cells was estimated from the amount of radioactivity incorporated during a 3 hr pulse with [$^3$H]thymidine. For each genotype, identical results were obtained with three other cell lines (data not shown).

FIG. (2B) Global genome repair (UDS) in primary mHR23A$^{+/+}$, mHR23A$^{+/-}$, and mHR23A$^{-/-}$ E13.5 MEFs. Cells were irradiated with 16 J/m$^2$ UV (254 nm) and labeled with [$^3$H]thymidine. Incorporation of radioactivity was measured by autoradiography and grain counting (average of 50 nuclei per cell line; the standard error of the mean is indicated). XPA$^{-/-}$ fibroblasts were measured as negative control. For each genotype, consistent results were obtained with three other independent cell lines (data not shown).

FIG. (2C) RNA synthesis recovery (RRS) after UV exposure of primary mHR23A$^{+/+}$, mHR23A$^{+/-}$ and mHR23A$^{-/-}$ E13.5 MEFs. Cells were UV irradiated (10 J/m$^2$, 254 nm) and allowed to recover for 16 hours. After a 1 hr pulse labeling with [$^3$H]uridine, cells were processed for autoradiography. The relative rate of RNA synthesis was expressed as the quotient of the number of autoradiographic grains over the UV-exposed nuclei and the number of grains over the nuclei of non-irradiated cells (average of 50 nuclei per cell line; the standard error of the mean is indicated). CSB$^{-/-}$ cells were used as a negative control. For each genotype, three other independent lines were assayed with similar outcome (data not shown).

FIG. (2D) UV survival of E8.5 MEF lines of wild-type, XPC$^{-/-}$, mHR23A$^{-/-}$/B$^{+/-}$, mHR23A$^{+/-}$/B$^{-/-}$, and mHR23A$^{-/-}$/B$^{-/-}$ (DKO).

FIG. (2E) UV-induced UDS in wild-type, XPC$^{-/-}$ and DKO E8.5 MEFs.

FIG. (2F) RNA synthesis recovery after UV irradiation of wild-type, XPC$^{-/-}$ and DKO E8.5 MEFs. For details for panels D-F see legends to panels A-C respectively and Experimental Procedures. Two independent experiments using two other DKO cell lines (before the cultures extinguished, not shown) showed a similar effect on UDS and RNA synthesis recovery.

Figure 3:
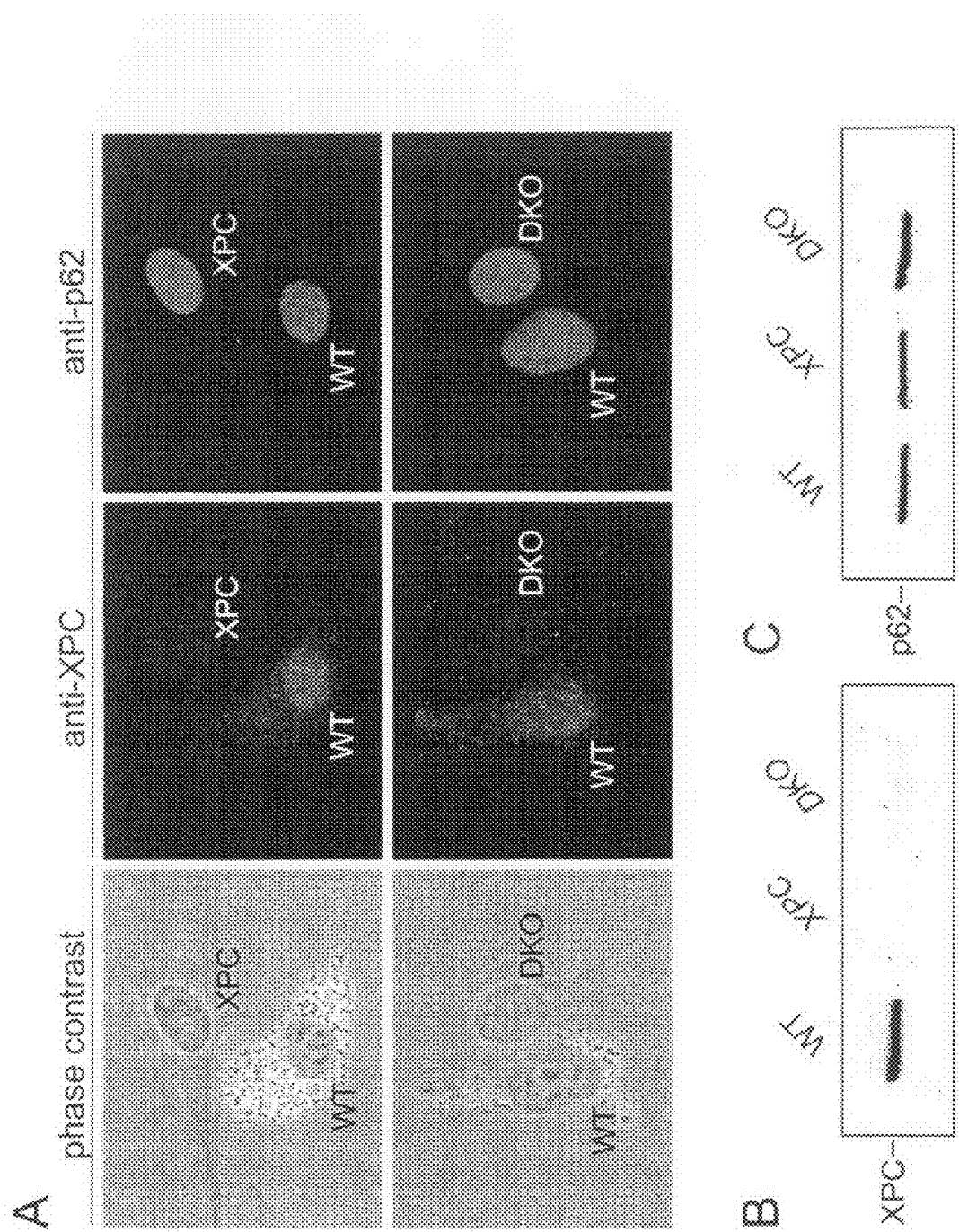

FIGS. 3A-3C. XPC expression in DKO E8.5 MEFs.

FIG. (3A) Phase contrast (left panels) and epifluorescence (middle and right panels) images of fixed wild-type (WT, labeled with latex beads), XPC$^{-/-}$ (XPC) and mHR23A$^{-/-}$/B$^{-/-}$ (DKO) MEFs. Cells were fixed by paraformaldehyde, permeabilized by 0.1% triton X-100, and subsequently immunolabeled with affinity-purified polyclonal antibodies against the human XPC protein (middle panels; stained with goat anti-rabbit Alexa 488-labeled secondary antibody). Monoclonal antibodies recognizing p62 subunit of TFIIH (right panels; stained with goat anti-mouse Cy3-labeled secondary antibody) were used as an internal control. All images were taken at the same magnification.

FIGS. (3B-C) Immunoblot analysis of XPC protein in cellular extracts from wild-type, XPC$^{-/-}$ and DKO E8.5 MEFs using polyclonal anti-human XPC antibodies (B). Monoclonal anti-p62 antibodies were used as an internal reference for the amount of protein in each lane (C).

FIGS. 4A-4F. Characterization of DKO cells expressing hHR23B and XPC-GFP.

(4A) UV survival of wild-type, XPC$^{-/-}$, DKO, and DKO MEFs cotransfected with: hHR23B (h23B), human XPC-GFP (hXPC), and h23B and hXPC-GFP cDNAs. Cells were exposed to different doses of UV (254 nm). After 4-5 days, the number of proliferating cells was estimated from the amount of radioactivity incorporated during a 3 hr pulse with [$^3$H]thymidine. For details see Experimental Procedures. For each cDNA construct, similar results were obtained with at least two other independent stably transfected cell lines (data not shown).

FIG. (4B) Schematic representation of XPC-EGFP-His6HA-N3 fusion protein (1208 aa). Indicated are the human XPC protein (940 aa), the enhanced green fluorescent protein tag (EGFP; 238 aa), and the hexameric histidine (SEQ ID NO. 21)-hemagglutinin double epitope tag (His6HA; 17 aa).

FIG. (4C) Immunoblot analysis of XPC expression in cellular extracts of WT (lane 1), XPC (lane 2), DKO (lane 3), and DKO MEFs cotransfected with: h23B (lane 4), hXPC-GFP (lane 5), and h23B and hXPC-GFP (lane 6) cDNAs, using a polyclonal antibody against the C-terminus of human XPC (upper panel). Monoclonal anti-p62 antibodies were used as a loading control (lower panel).

FIG. (4D) Phase contrast (left) and epifluorescence (right) images of fixed WT (labeled with latex beads) and DKO cells cotransfected with hHR23B cDNA. Cells were fixed by paraformaldehyde, followed by 0.1% triton X-100 permeabilization and subsequently immunolabeled with affinity-purified polyclonal anti-human XPC (right; stained with goat anti-rabbit Alexa 488-labeled secondary antibody). Monoclonal anti-p62 antiserum was used as an internal control (stained with goat anti-mouse Cy3-labeled secondary antibody; data not shown). Images were taken at the same magnification. Similar results were obtained with DKO cells cotransfected with hXPC-GFP, and hHR23B and hXPC-GFP cDNAs (not shown).

FIGS. (4E-4F) Phase contrast (left panels) and epifluorescence (right panels) images of living DKO cells cotransfected with: hXPC-GFP (E), or hHR23B and hXPC-GFP (F) cDNAs. All images were taken at the same magnification. Shown are the nucleus of a first cell (numbered 1) and the nucleus of a second cell (numbered 2).

FIGS. 5A-5E. Effect of UV, NA-AAF, and proteasome inhibitor on hHR23B-dependent XPC-GFP level in living DKO cells.

FIG. (5A) Kinetic analysis of living DKO cells expressing XPC-GFP/hHR23B upon 10 J/m$^2$ UV-C in time over a period of 30 hours. Percentage XPC-GFP: the percentage of GFP-expressing fluorescent cells of the total number of cells.

FIG. (5B) Immunoblot analysis of DKO cells expressing XPC-GFP/hHR23B before exposure to damaging agent (lane 1), 6 hr after exposure to 10 J/m$^2$ UV-C (lane 2), and 6 hr after treatment with 10 μM CBZ-LLL (lane 3) using monoclonal antibodies recognizing the HA epitope of XPC-GFP (upper panel). A monoclonal antibody against the p62 subunit of TFIIH (lower panel) was used as a loading control. A similar outcome was obtained with two other independent DKO cell lines expressing XPC-GFP/hHR23B (data not shown).

FIG. (5C) Combined phase contrast and fluorescence images (upper panels), and epifluorescence images (lower panels) of the same living DKO cells expressing XPC-GFP/hHR23B before UV (left panels) and 6 hr after 10 J/m$^2$ UV-C (right panels). White arrows indicate the scratch mark on glass coverslips. Numbers represent the same living cells before and after UV exposure. Identical results were obtained with two other independent DKO cell lines expressing XPC-GFP/hHR23B (data not shown). All images were taken at the same magnification. Shown are the nuclei of three DKO cells (numbered 1, 2, and 3).

FIG. (5D) Combined phase contrast and fluorescence images (upper panels), and epifluorescence images (lower panels) of living DKO cells expressing XPC-GFP/hHR23B before NA-AAF (left panels) and 8 hr after 50 µM NA-AAF (right panels). White arrows indicate the scratch on glass coverslips. The numbers represent the corresponding living cells on coverslips before and after NA-AAF treatment. Identical results were obtained with two other independent DKO cell lines expressing XPC-GFP/hHR23B (data not shown). All images were taken at the same magnification. Shown are the nuclei of five DKO cells (numbered 1, 2, 3, 4, and 5).

FIG. (5E) Combined phase contrast and fluorescence images (upper panels), and only epifluorescence images (lower panels) of living DKO cells expressing XPC-GFP/hHR23B before treatment with proteasome inhibitor CBZ-LLL (left panels) and 6 hr after 10 µM CBZ-LLL (right panels). All images were taken at the same magnification.

Figure 6:
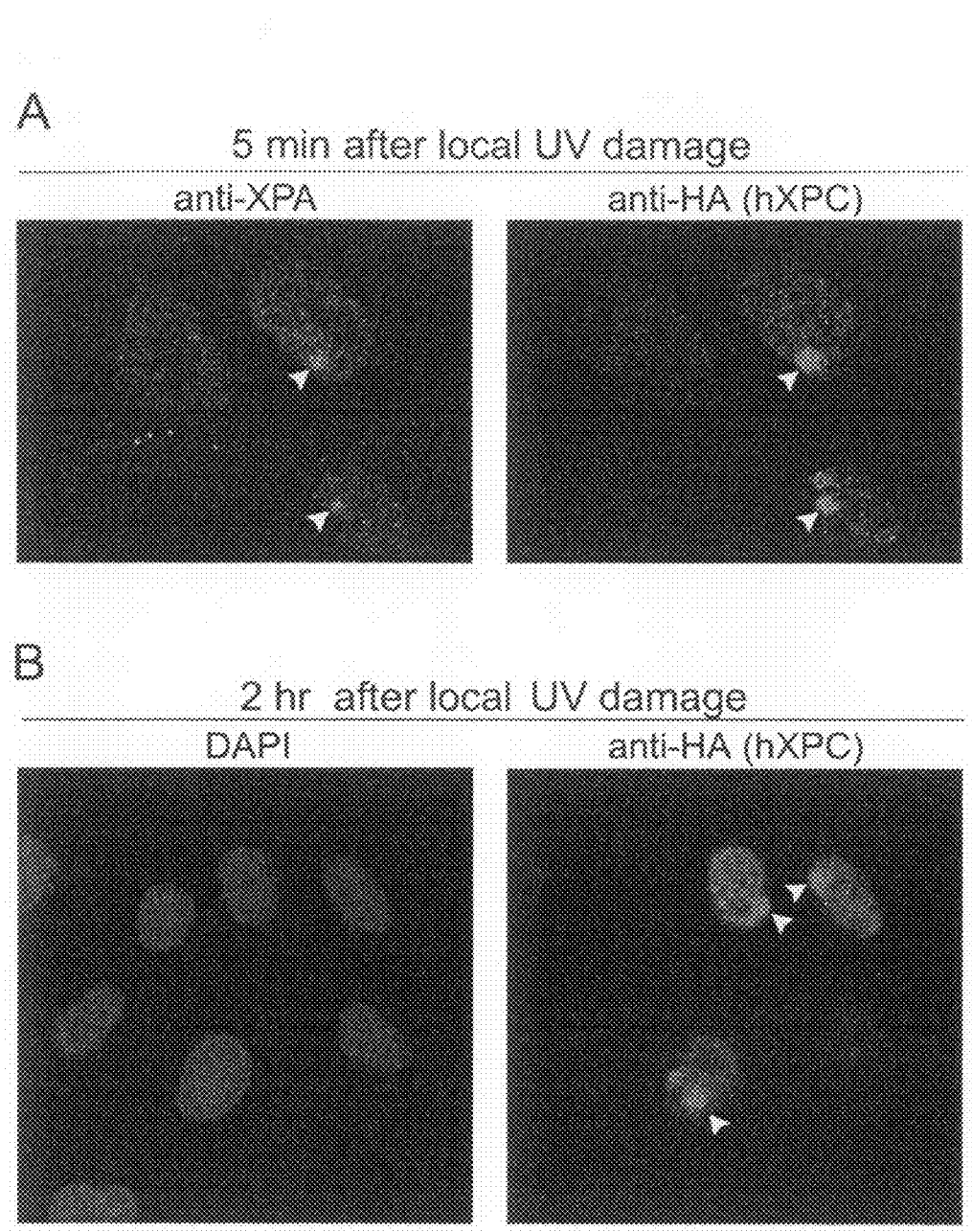

FIGS. 6A-6B. Local UV damage induces overall XPC stabilization in nuclei of DKO cells expressing XPC-GFP/hHR23B.

(FIGS. 6A-B) DKO cells expressing XPC-GFP/hHR23B were exposed to 64 J/m$^2$ UV-C through 5.0 µm pore filters and fixed 5 min (A) and 2 hours (B) later with paraformaldehyde. Double immunofluorescent labeling using antibodies against XPA (A, left panel; stained with goat anti-rabbit Alexa 488-labeled secondary antibody) and HA epitope (A, right panel; stained with goat anti-rat Alexa 594-labeled secondary antibody). DAPI stained (B, left panel) and epifluorescence images without antibody labeling (B, right panel). Arrows indicate the site of UV-induced local damage in the nuclei of DKO cells expressing hXCPC-GFP/hHR23B. Note: Compare the increased fluorescence signal over the entire nucleus of damaged cells to the signal of non-damaged nuclei for overall stabilization of XPC (B).

Figure 7:
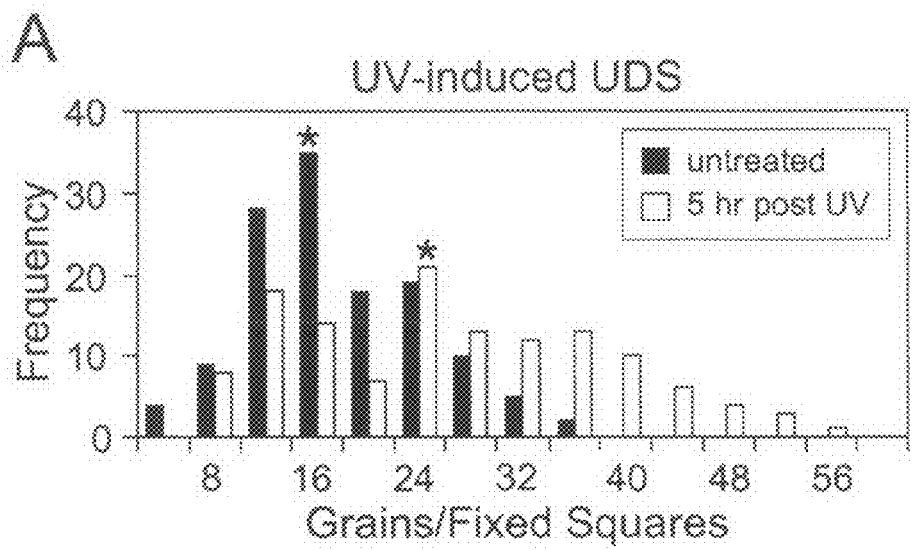
Figure 7:
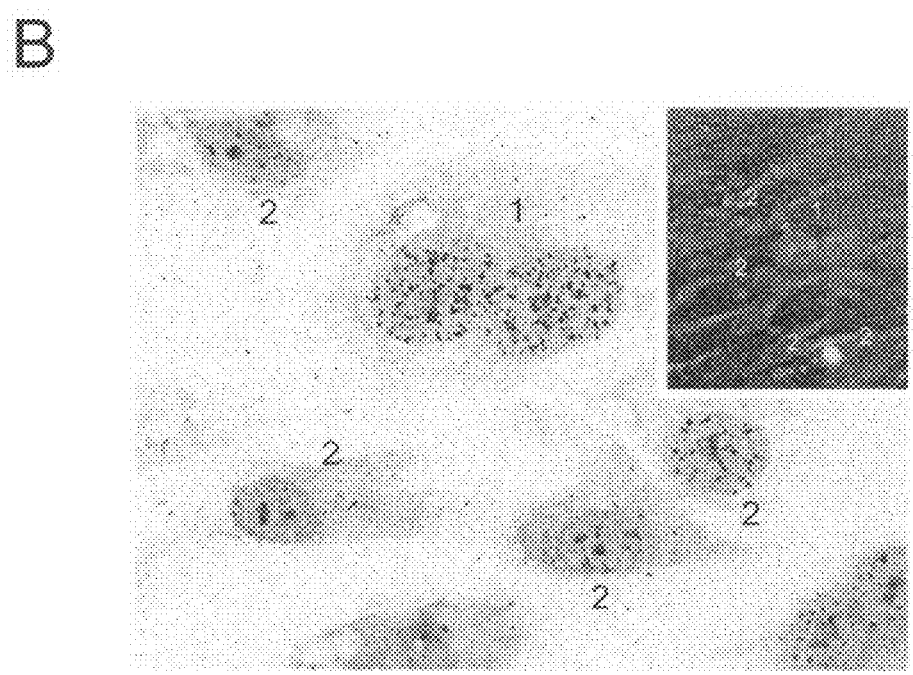

FIGS. 7A-7B. Enhanced DNA repair correlates with high levels of XPC in UV-induced UDS in DKO cells expressing XPC-GFP/hHR23B.

FIG. (7A) Histogram of UV-induced UDS in DKO cells expressing XPC-GFP/hHR23B. Five hours after exposure to 10 J/m$^2$ UV-C, cells were subsequently irradiated with 16 J/m$^2$ UV-C and labeled with [$^3$H]thymidine for 1 hr (white columns, mean of UDS level is 25±SEM 1). In parallel, non-prechallenged cells only exposed to 16 J/m$^2$ UV-C were used as controls (black columns, mean of UDS level is 16±SEM 0.6). Asterisks indicate the mean values of the UDS levels. Incorporation of radioactivity was measured by autoradiography and grain counting (130 fixed squares counted per cell line and each square represented approximately 50% of the nucleus surface). UV-induced UDS of wild-type (mean 17±SEM 0.8) fibroblasts were measured as controls (data not shown).

FIG. (7B) Effect of microinjection of XPC-GFP cDNA on UV-induced UDS in human wild-type (C5RO) fibroblasts. Shown is a micrograph of a wild-type homodikaryon (numbered 1) microinjected with XPC-GFP in one of the nuclei and subjected to UV-induced UDS. Prior to UDS, fluorescence images were captured (inset in B). The injected cell has a considerably larger number of grains above its nuclei than the noninjected, surrounding mononuclear cells (numbered 2).

FIGS. 8A-8D. Evidence for XPC shuttling between nucleus and cytoplasm.

FIG. (8A) Schematic representation of human XPC protein (940 aa), indicating three putative leucine-rich nuclear export signals (NES), three putative nuclear location signals (NLS), an N-terminal acidic stretch, a central Serine-rich domain, and a C-terminal HR23-binding region (Uchida et al., 2002). The consensus sequence for NES is indicated separately. Although originally defined as leucine-rich, other hydrophobic residues (I, F, V, M) have been shown to be able to substitute for leucines in functional NES sequences of various proteins (Mowen and David, 2000; Roth et al., 1998).

FIG. (8B) Amino acid sequence comparison between mouse and human XPC NES-like domains. Numbers indicate the location of the amino acids within the respective proteins. Closer examination of NES2 and NES3 revealed multiple conserved leucine-rich regions.

FIGS. (8C-D) Heterokaryon nuclear-cytoplasmic shuttling assay using DKO cells expressing XPC-GFP(His$_6$HA)/hHR23B and HeLa cells. Six hours prior to cell fusion, cells were exposed to 10 J/m$^2$ UV-C. After cell fusion, cells were cultured either in the absence (C) or in the presence (D) of the nuclear export inhibitor LMB (10 ng/ml). Four hours after fusion, cells were fixed and immunostained with anti-HA (left) to detect the fusion protein and anti-hERCC1-specific antibody (middle) to recognize HeLa cells. The right picture is a phase contrast image of the same cells. For clarity, mouse nuclei were marked by (1) and human (HeLa) nuclei were marked by (2).

Figure 9:
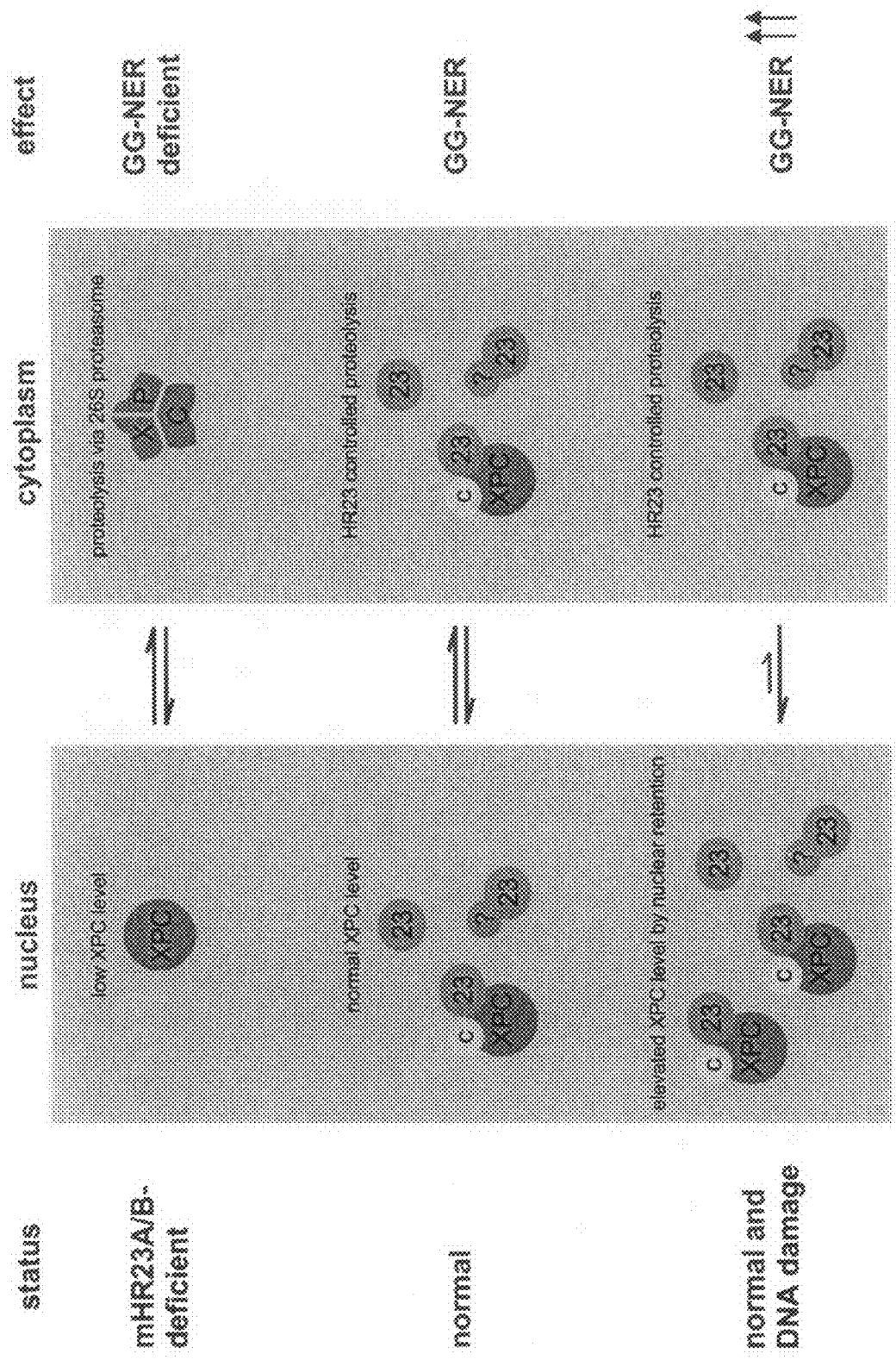

FIG. 9. Model for the DNA damage and HR23-dependent regulation of XPC and GG-NER. In the total absence of the HR23 proteins (mHR23A/B-decifient), XPC is intrinsically unstable and targeted for ubiquitin-dependent proteolysis via the 26S proteasome. In view of the parallel with p53 nucleocytoplasmic shuttling, it was postulated that XPC is degraded in the cytoplasm. As a consequence, the steady-state level of XPC is decreased, resulting in reduced GG-NER capacity (upper panel). Under normal conditions, HR23 proteins (indicated as 23) control XPC degradation leading to partial stabilization of XPC (in a complex with HR23 and CEN2 (C)). Higher steady-state levels of XPC result in proficient GG-NER (middle panel). NER-type DNA damage (e.g., UV irradiation) induces a further increase in XPC/HR23/CEN2 protein levels through nuclear retention of XPC bound to lesions, and accordingly enhances GG-NER capacity (lower panel). A comparable HR23-mediated stabilization mechanism may hold for other factors and cellular pathways in which HR23 proteins are implicated (see discussion for further explanation).

DESCRIPTION OF THE PREFERRED EMBODIMENTS

Preferably, the DNA lesion comprises a lesion that is a substrate for global genome nucleotide excision repair and/or base excision repair. More preferably, the HR23 protein-binding molecule comprises xeroderma pigmentosum group C protein, 3-methyladenine DNA glycosylase, CREB, p53, or a functional part, derivative and/or analogue thereof.

Xeroderma pigmentosum group C (XPC) protein is involved in a DNA repair mechanism called nucleotide excision repair (NER). NER primarily focuses on helix-distorting injuries, including UV-induced cyclobutane pyrimidine dimers (CPD) and pyrimidine (6-4) pyrimidone photoproducts (6-4PP), as well as numerous chemical DNA adducts (Friedberg et al., 1995). Inherited defects in NER are the cause of several severe diseases, such as the cancer-prone syndrome xeroderma pigmentosum (XP). Patients are characterized by extreme sun sensitivity, sun-induced pigmentation anomalies, and a >2000-fold predisposition to UV-induced skin cancer. Moreover, an impaired DNA repair mechanism such as NER or BER (described below) is involved in alteration of cells and their response to genotoxic agents.

NER entails a multistep reaction and requires the coordinated action of ~30 proteins implicated in damage detection, helix opening, lesion verification, dual incision of the damaged strand bracketing the injury, removal of the 25-30 base damage-containing oligonucleotide, gap-filling DNA synthesis and ligation (Hoeijmakers, 2001). Two NER subpathways exist: global genome NER (GG-NER), operating genome wide and transcription-coupled repair (TCR), focusing on transcription-blocking lesions in the transcribed strand of active genes (Hanawalt, 2000). Most XP genes are implicated in both NER subpathways, but XPC-deficient cells are unique in being selectively deficient in GG-NER.

3-Methyladenine DNA glycosylase (MAG) is involved in a DNA repair mechanism called base excision repair (BER). BER corrects base alterations induced by endogenous and/or exogenous oxidative events, ionizing radiation and small alkylating agents.

Examples of potentially mutagenic BER lesions are 8-oxoguanine, $O^6$-methylguanine, deaminated methylated cytosine and thymine glycol. Base excision repair is initiated by MAG and several other glycosylases. Accumulating evidence implicates unrepaired BER lesions in the aging of somatic cells.

According to the present invention, a DNA lesion in a eukaryotic cell results in accumulation of an HR23 protein-binding molecule within the cell. For instance, an NER- and/or BER-sensitive DNA lesion results in rapid accumulation of XPC and/or MAG of a eukaryotic cell, especially in the nucleus. Accumulation of an HR23 protein-binding molecule, such as XPC and/or MAG, is at least in part due to the fact that the HR23 protein-binding molecule is stabilized by the chaperone proteins HR23A and/or HR23B if a DNA lesion is present. Both chaperone proteins are normally present in eukaryotic cells. In terms of the invention, a "HR23 protein" is defined as an HR23A or HR23B protein. It has been shown by the present inventors that only one of them suffices for stabilizing XPC. If no NER- or BER-sensitive DNA lesion is present, XPC and MAG are rapidly degraded. A complex comprising HR23 and an HR23 protein-binding molecule is involved in DNA repair. For instance, a complex comprising XPC and HR23 performs a damage-sensing step within GG-NER, triggering subsequent association of the NER-involved proteins TFIIH, XPG, XPA, RPA, and ERCC1/XPF. Accumulation of XPC, or a functional part, derivative and/or analogue thereof, is therefore indicative for the presence of a DNA lesion that is a substrate for GG-NER.

As another example, HR23 is also capable of associating with MAG. Since MAG plays an important role in an initiation of a BER response, accumulation of MAG, or a functional part, derivative and/or analogue thereof, is indicative of the presence of a DNA lesion that is a substrate for BER.

A number of other binding partners for at least one of the HR23 proteins are found, including cell cycle checkpoint proteins such as CREB and p53 as well as proteins implicated in mitosis. These binding partners are also suitable for a method of the invention.

HR23A and HR23B are homologues of the *Saccharomyces cerevisiae* gene RAD23. The present inventors have cloned the two human homologues of RAD23, designated hHR23A and hHR23B. HR23 proteins contain a ubiquitin-like (Ubl) N-terminus and two ubiquitin-associated (UBA) domains pointing to multiple links with the ubiquitin system. The Ubl domain of yeast RAD23 is important for UV survival and for interaction with the 26S proteasome, whereas the UBA domains enable binding to ubiquitin. Until the present invention, the functional relationship between RAD23, DNA repair and the ubiquitin system was unclear.

Now that it has been found that HR23 protein-binding proteins such as XPC and MAG accumulate in a eukaryotic cell upon a DNA lesion, a rapid and sensitive test is provided. A method of the invention is preferred over the widely used Ames test, because readout is based on the detection of accumulation of an HR23 protein-binding molecule (for instance, by way of fluorescence) and not on bacterial growth. A method of the invention can be performed quicker and allows for smaller quantities of a test compound as compared to the Ames test. Preferably, a method of the invention is performed within 3 to 6 hours. Moreover, a method of the invention provides more information about the effect of a test compound upon a eukaryotic organism as compared to the Ames test. For instance, information is provided about transport of a test compound into a eukaryotic cell and into the nucleus of such cell, possible enzymatic modification of the test compound by a eukaryotic organism, and susceptibility of eukaryotic DNA. Moreover, a test of the invention provides information about the type of DNA damage induced by an agent, since different types of DNA lesions involve accumulation of specific HR23 protein-binding molecules.

Potentially mutagenic or cytotoxic agents can be tested by exposing a eukaryotic cell to the agent and determining whether an HR23 protein-binding molecule such as XPC and/or MAG, or a functional part, derivative and/or analogue thereof, accumulates within the cell. In terms of the invention, by "an agent capable of inducing a DNA lesion" is meant an agent, such as for instance a compound or radiation, which is capable of inducing at least one DNA lesion. By "an agent capable of inducing a DNA lesion that is a substrate for GG-NER and/or BER" is meant an agent, such as for instance a compound or radiation, which is capable of inducing at least one DNA lesion that is normally recognized by a GG-NER and/or BER system. By "normally recognized" is meant that in a (preferably naturally occurring) cell with functioning GG-NER and/or BER system, such lesion is recognized by the GG-NER and/or BER system. Of course, a capability of inducing DNA lesions often strongly depends on the dose of compound/radiation. Therefore, it is often suitable to test several amounts of test compound or several intensities of radiation with a method of the invention. However, if it is only questioned whether a specific dose of compound/radiation (for instance, present in a new chemical compound, in a new procedure of purification, or in, for example, soiled ground) is mutagenic, a test of the invention can be performed with only that dose.

A eukaryotic cell can be exposed to an agent in many different ways, which are known in the art. For instance, a potentially mutagenic compound can be administered to a culture comprising the eukaryotic cell. Alternatively, the compound can be administered to a non-human animal comprising the cell. Alternatively, a eukaryotic cell, for instance, as part of a cell line or as part of a non-human animal, can be exposed to radiation. In one embodiment, several different doses of compound/radiation are used.

With a method of the invention, accumulation of an intact XPC and/or MAG protein in a eukaryotic nucleus can be determined. Alternatively, accumulation of a functional part, derivative and/or analogue of XPC and/or MAG can be tested. In a preferred embodiment, the XPC protein comprises a human XPC protein or a functional part, derivative and/or analogue thereof.

A functional part, derivative and/or analogue of an XPC and/or MAG protein can be provided to a eukaryotic cell with conventional methods known in the art, such as microinjection or transfection procedures. Such functional part, derivative and/or analogue can be provided to a eukaryotic cell by use of a nucleic acid encoding the functional part, derivative and/or analogue. Of course, the nucleic acid is preferably suitable for expression within the cell. As shown in the examples, it is also possible to provide a cell with a nucleic acid encoding a whole XPC and/or MAG protein. The protein may be an endogenous XPC and/or MAG protein, or may be derived from a different kind of organism.

In a preferred embodiment, the HR23 protein-binding molecule is labeled to allow for easy detection. In one preferred embodiment, the label comprises green fluorescent protein (GFP) or luciferase. If GFP is used as a label, accumulation of an HR23 protein-binding molecule such as XPC and/or MAG can be easily detected with a microscope or a fluorescent activated cell sorter (FACS) for easy and rapid quantitative readout. An HR23 protein-binding molecule can be labeled in many different ways and with many different labels known in the art. For instance, the label may be coupled to the molecule by way of a (flexible) linker. The linker can be a peptide.

The label can also be linked to the molecule in the form of a fusion protein, comprising both the molecule and the label. A nucleic acid can be constructed encoding such fusion protein by methods known in the art. Of course, the person skilled in the art can think of alternative ways of linking a label to XPC and/or MAG, or to a functional part, derivative and/or analogue thereof.

Besides labeling of an HR23 protein-binding molecule, accumulation of the molecule can also be detected in different ways that are known in the art. For instance, an antibody directed towards the molecule can be used. Binding of the antibody can be detected by staining the antibody, an affinity column may be used, etc. As another possibility, the molecule can be rendered radioactive.

A functional part of an XPC and/or MAG protein is defined as a part which has the same kind of properties as XPC and/or MAG in kind, not necessarily in amount. A functional part of XPC and/or MAG is, for instance, also capable of binding to HR23A and/or HR23B, and/or capable of entering the nucleus of a eukaryotic cell, optionally when bound to HR23A or HR23B. A functional derivative of an XPC and/or MAG protein is defined as a protein which has been altered such that the properties of the molecule are essentially the same in kind, not necessarily in amount. A derivative can be provided in many ways, for instance, through conservative amino acid substitution.

A person skilled in the art is well able to generate analogous compounds of an XPC and/or MAG protein. This can, for instance, be done through screening of a peptide library. Such analogue has essentially the same properties of an XPC and/or MAG protein in kind, not necessarily in amount.

As used herein, "an XPC protein" and "XPC" are used interchangeably and can also mean a functional part, derivative and/or analogue of an XPC protein. Likewise, "a MAG protein" and "MAG" are used interchangeably herein and can also mean a functional part, derivative and/or analogue of a MAG protein.

In a preferred embodiment, a method of the invention is provided wherein the eukaryotic cell is overexpressing HR23A and/or HR23B protein, or a functional part, derivative and/or analogue thereof. As shown in the examples, very good results are obtained if HR23A and/or HR23B is overexpressed. Overexpression of HR23A and/or HR23B can be performed in different ways. For instance, a nucleic acid encoding HR23A and/or HR23B can be constructed, preferably with a strong promoter. Such nucleic acid may comprise several copies of a gene encoding HR23A and/or HR23B. Overexpression of HR23A and/or HR23B can be induced by administration of the nucleic acid to a cell capable of expressing the nucleic acid. In one embodiment, the nucleic acid encodes human HR23A and/or human HR23B protein or a functional part, derivative and/or analogue thereof. In another embodiment, the nucleic acid encodes murine HR23A and/or murine HR23B protein or a functional part, derivative and/or analogue thereof.

The nucleic acid may be expressed in a eukaryotic cell in addition to endogenously expressed HR23A and/or HR23B. Alternatively, the cell may be rendered deficient of endogenous HR23A and/or HR23B. The nucleic acid preferably comprises a stronger promoter than the endogenous genes of HR23A and/or HR23B, enabling the cell to overexpress HR23A and/or HR23B.

In one embodiment, a method of the invention is provided wherein the eukaryotic cell is a mammalian cell. Preferably, the cell is a murine cell, more preferably a mouse embryonic fibroblast. The cell can be part of a cell line, such as a mouse embryonic fibroblast cell line. According to one embodiment, the cell is deficient in endogenous HR23A and/or HR23B protein. The cells of the cell line are also preferably deficient in endogenous HR23A and/or HR23B protein. Murine HR23A or HR23B protein is called mHR23A or mHR23B. A cell which is deficient for both endogenous HR23A and HR23B protein is preferably artificially provided with HR23A and/or HR23B. As disclosed in the examples, only one kind of HR23 protein is sufficient to preserve GG-NER activity. In another preferred embodiment, a method of the invention is provided wherein the XPC protein or a functional part, derivative and/or analogue thereof comprises a human XPC protein or a functional part, derivative and/or analogue thereof.

The invention also provides a method for screening of agents capable of at least in part inhibiting a cellular process that normally results in accumulation of HR23 protein-binding molecules. For instance, in response to a DNA lesion, an HR23 protein-binding molecule accumulates within a cell. This involves many cellular processes, such as RNA synthesis, RNA processing, RNA transport, and/or RNA translation. If an agent is capable of inhibiting such process, accumulation of an HR23 protein-binding molecule will not occur or will occur less when a DNA lesion is present. The invention therefore provides a method for determining whether an agent is capable of at least in part inhibiting a cellular process, such as proteolysis, nucleo-cytoplasma shuttling, RNA synthesis, RNA processing, RNA transport, and/or RNA translation, the process resulting in accumulation of HR23 protein-binding molecule within a cell, comprising:

exposing at least one eukaryotic cell to the agent; and
determining whether an HR23 protein-binding molecule accumulates therewithin. Preferably, the eukaryotic cell comprises a DNA lesion.

In a preferred embodiment, the HR23 protein-binding molecule comprises xeroderma pigmentosum group C protein, 3-methyladenine DNA glycosylase, CREB, p53, or a functional part, derivative and/or analogue thereof.

Preferably, the proteolysis comprises proteasomal proteolysis. It has been shown by the present inventors that hXPC-GFP is mainly degraded via ubiquitin/proteasome-dependent proteolysis.

In one aspect, the invention provides a mammalian cell which is deficient in endogenous HR23A protein or endogenous HR23B protein. In one embodiment, the cell comprises a murine cell, preferably a mouse embryonic fibroblast. With a cell of the invention, a cell line can be generated. Such cell line is suitable for high throughput tests of compounds, for instance, potentially mutagenic or cytotoxic compounds or compounds potentially capable of inhibiting proteolysis, with a method of the invention.

A cell line comprising a cell of the invention is therefore also herewith provided.

As outlined in the examples, a non-human animal comprising a cell of the invention is also very suitable for testing and investigation purposes. The invention therefore also provides a non-human eukaryotic organism which is deficient in endogenous HR23A protein and/or endogenous HR23B protein. Since total HR23 deficiency is incompatible with animal life, an animal of the invention should comprise HR23, either one of the endogenous HR23A or HR23B proteins or a functional part, derivative and/or analogue thereof, or an exogenous (such as human or murine) HR23 protein or a functional part, derivative and/or analogue thereof. In one embodiment, the animal is provided with an exogenous controllable HR23 transgene. The invention also provides a non-human animal of the invention with compromised (endogenous) HR23 functions in a conditional fashion.

According to the invention, an HR23 protein-binding molecule accumulates in a cell in response to a DNA lesion. For instance, XPC and/or MAG accumulate(s) in a eukaryotic cell in response to a DNA lesion that is a substrate for GG-NER and/or BER. This applies to cells with a functioning GG-NER and/or BER system. However, if a cell's GG-NER and/or BER system is essentially impaired, XPC and/or MAG will not accumulate in the nucleus in response to DNA damage. Hence, accumulation of an HR23 protein-binding molecule in a cell that is exposed to a DNA-affecting agent is indicative of an essentially functioning DNA repair system. The invention therefore provides a method for determining whether a cell has an at least partly impaired DNA repair system, comprising:
exposing the cell to an agent capable of inducing a DNA lesion; and
determining whether an HR23 protein-binding molecule accumulates within the cell. Preferably, the HR23 protein-binding molecule comprises xeroderma pigmentosum group C protein and/or 3-methyladenine DNA glycosylase, or a functional part, derivative and/or analogue thereof.

Impaired NER and/or BER activity is associated with severe disorders, such as xeroderma pigmentosum (XP), cockayne syndrome (CS) and trichothiodystrophy (TTD).

Xeroderma pigmentosum is due to a mutation in one of seven genes involved with NER (designated XPA to XPG). Parchment skin (xeroderma) and freckles (pigmentosum) are the prominent cutaneous hallmarks of XP patients. These manifestations are strikingly restricted to sun-exposed areas of their skin. Typically, sun exposure of XP patients causes a progressive degenerative alteration of the skin and eyes, beginning as early as the age of 2 years. Furthermore, XP is associated with an elevated frequency (>1000-fold) of sunlight-induced skin cancers, which are also largely confined to sun-exposed areas like the face, neck, head and even the tip of the tongue. XP patients mainly develop basal cell or squamous cell carcinomas, seen in at least 45% of all XP patients, many of whom often have multiple primary neoplasms, and less frequently melanomas (5% of patients). The mean age of onset for skin neoplasms is 8 years, which is about 50 years earlier than in the general population. The main cause of death in XP individuals is neoplasia, which reduces the lifespan by approximately 30 years. XP patients also have a 10- to 20-fold increased risk of developing several types of internal cancers before the age of 20 years. Abnormalities in the immune system detected in XP patients are likely to contribute to the development of (skin) tumors.

A fraction of XP patients (~18%) displays progressive neurologic degeneration secondary to a loss of neurons. This feature seems to be related to the significance of the NER defect. For example, XPC patients, who only have the GG-NER defect, usually do not develop neurologic abnormalities, and if so, symptoms appear much later in life compared to TC-NER-defective XPD and completely NER-deficient XPA patients. A possible explanation for the onset of neurologic abnormalities in XP individuals is that defective DNA repair of endogenous, oxidative NER lesions in neurons triggers cell death.

The genetic heterogeneity of XP patients is accompanied by heterogeneity in severity of the repair defect and of the consequent symptoms. The most severely affected patients are XPA, XPB, XPD and XPG individuals. The two most common forms of XP are XPA and XPC. The group of XPD patients is the most heterogeneous, with a level of residual repair synthesis between 15 and >50%. Furthermore, XPF patients are moderately UV sensitive and show intermediate repair synthesis, indicative of mutations that lead to poor but not complete abolishment of NER. This could be due to the anticipated dual function of the ERCC1-XPF complex in NER and recombination repair. A null allele for ERCC1 or XPF and the consequential defect of cross-link repair are predicted to be incompatible with life. All XP patients of complementation groups A to G are defective in both NER subpathways, with the exception of XPC and XPE whose NER defect is limited to GG-NER. The susceptibility to sunburn of XPC patients is no different from normal individuals, indicating that TC-NER alone is sufficient to prevent this acute response to UV exposure. XPC cells have a residual UDS level of 15-30% due to functional TC-NER and are therefore less sensitive to UV than XPA or XPD cells. Patients in the XP-variant group have mild to severe skin symptoms and usually display a normal functioning central nervous system. Unlike classical XP, XPV patients show a normal level of NER activity but lack the capacity to efficiently replicate damaged DNA, leading to error-prone replication and a hypermutable phenotype. This phenotype, together with the increased frequencies of genomic rearrangements observed in XPV cells, may cause the elevated sun-induced carcinogenesis seen in these patients.

Cockayne Syndrome (CS)

CS is a very pleiotropic disorder characterized by cutaneous photosensitivity (with or without thin or dry skin and hair), severe postnatal growth failure (cachectic dwarfism), mental retardation, and progressive neurologic dysfunction. CS cells are sensitive to a number of DNA-damaging agents (including UV) due to a defect in TC-NER. In contrast to patients suffering from the prototype NER-deficient disorder XP, CS individuals are not predisposed to skin cancer. Other common CS symptoms include sensorineural hearing loss, progressive ocular abnormalities (such as pigmentary retinopathy and/or cataracts), wizened bird-like faces, impaired sexual development, skeletal abnormalities (typically resulting in short stature), dental caries, kyphosis (hunchback), and premature osteoporosis (demineralization). The progressive neurological degeneration has a very early onset in CS individuals (beginning around 2 years of age) and is caused by dysmyelination. The mean age of death in CS is 12.5 years and mainly secondary to pneumonia, which in turn could be due to the generally poor condition of the patients. Clearly, CS clinical symptoms are much more severe than the classical XP condition and go beyond photosensitivity. Photosensitivity and other XP-like features (such as pigmentation abnormalities and predisposition to skin cancer) can be attributed to the NER defect. However, the severe development and neurological manifestations of CS cannot be explained by NER. The transcriptional engagement of CSA and CSB (analogous to XPB and XPD) suggests that transcription deficiency, perhaps induced by DNA damage, also contributes to the clinical pictures. In some cases, CS features are found in combination with XP, due to specific mutations in the XPB, XPD or XPG genes. Cells from CSA, CSB and XPG individuals with severe CS symptoms are slightly sensitive to ionizing radiation in addition to UV light. It is hypothesized that inefficient TCR of oxidative lesions (e.g., thymine glycol) which block transcription underlies this ionizing radiation sensitivity although ionizing radiation is a poor inhibition of transcription in general. This indicates an additional role of CSA, CSB and XPG in coupling arrested transcription with both BER and NER, and suggests a general repair-transcription coupling deficiency as the major cause of the extensive variations in symptoms and severity of the CS phenotype. The developmental defects and the premature aging-related symptoms of CS can be attributed to the incomplete repair of endogenous oxidative damage, which in turn causes cellular malfunction and/or induction of apoptosis. The defective TCR in CS cells enhances their p53-dependent apoptotic response, contributing to the elimination of cells that potentially carry oncogenic mutations. This explains the lack of cancer predisposition in CS after UV exposure. Numerous other CS-like patients have been identified, for example, CAMFAK (for cataracts, microcephaly, failure to thrive, kyphoscoliosis) and COFS (cerebro-oculofacial syndrome), but these patients fail to exhibit pronounced photosensitivity in spite of the fact that cells of the patients display defective recovery of RNA synthesis, suggesting the possibility of a partial transcription defect without the accompanying TC-NER defect of CS.

Trichothiodystrophy (TTD)

TTD is caused by neurectodermal dysplasia which causes a collection of symptoms referred to by the acronym PIBIDS: photosensitivity, ichthyosis, brittle hairs, intellectual impairment, decreased fertility, and short stature.

Skeletal abnormalities are also frequently observed, including a peculiar bird-like face, a receding chin, and retardation of skeletal age. Moreover, axial osteoschlerosis (abnormal hardening of the bone), peripheral osteoporosis and kyphosis have been reported. The striking ectodermal symptoms (brittle hair and dystrophic nails) are unique for TTD. However, the remainder of the clinical features are strikingly similar to CS, including the absence of cancer predisposition. The photosensitivity in TTD patients is due to a defect in NER caused by a mutation in one of three genes: XPB, XPD or TTDA. The NER defect in all but two of 20 studied UV-sensitive TTD families can be assigned to the XPD complementation group. Despite the NER defect, the pigmentation abnormalities are relatively mild compared to classical XP. The typical brittleness of TTD hair is caused by a substantial reduction in the content of hair-specific cysteine-rich matrix proteins that provide the hair shaft with its natural strength by cross-linking the keratin filaments. Growth retardation (cachectic dwarfism) in TTD patients is a very heterogeneous clinical symptom and—when severe—can be associated with death in early childhood. TTD, like CS, is considered to be a repair/transcription syndrome. Mutations in XPD may not only affect the NER function but also cripple transcription by TFIIH, accounting for the typical TTD and CS phenotypes. Consistent with this idea, all causative mutations in XPD have been found to be disease-specific. Recently, the phenotype of two unrelated TTDA patients was directly attributed to a limiting amount of TFIIH, probably secondary to a mutation in a gene determining the complex stability. A reduced TFIIH level has an effect on its repair function and also on its role in basal transcription.

A method of the invention is particularly suitable for determining whether an individual suffers from, or is at risk of suffering from, a disease associated with impaired DNA repair activity, such as XP, CS and/or TTD. With a method of the invention it can, for instance, be determined whether a cell from the individual has an at least partly impaired GG-NER and/or BER system. If the cell appears to have an impaired DNA repair system, it is indicative for disease.

In one embodiment, the invention therefore provides a method for determining whether an individual suffers from, or is at risk of suffering from, a disease related to an at least partly impaired DNA repair system, comprising:

obtaining at least one cell from the individual;
exposing the cell to an agent capable of inducing a DNA lesion; and
determining whether an HR23 protein-binding molecule accumulates within the cell. Preferably, the HR23 protein-binding molecule comprises xeroderma pigmentosum group C protein and/or 3-methyladenine DNA glycosylase, or a functional part, derivative and/or analogue thereof.

In a preferred embodiment, the disease comprises xeroderma pigmentosum, cockayne syndrome, and/or trichothiodystrophy.

A kit of parts comprising a cell and/or a cell line of the invention is also herewith provided. Preferably, a kit of parts of the invention comprises an agent capable of inducing a DNA lesion, such as a lesion that is a substrate for global genome nucleotide excision repair and/or base excision repair. More preferably, the kit of parts further comprises a detection system for detecting a change in level of an HR23 protein-binding molecule. Most preferably, the kit of parts comprises a detection system for detecting a change in level of XPC, MAG, CREB, p53, or a functional part, derivative and/or analogue thereof. A kit of parts of the invention is particularly suitable for performing a method of the invention.

According to the invention, XPC, MAG and HR23 play an important role in the GG-NER and BER systems. Deficiency of at least one of these proteins is, therefore, challenging for an organism's NER and/or BER system. Such deficiencies can, at least partly, be overcome by providing at least one cell from an individual with at least one of the proteins. Likewise, other DNA repair deficiencies can be overcome by providing at least one cell from an individual with at least one HR23 protein-binding molecule. Preferably, the protein is provided by gene therapy. The invention thus provides a method for treating a disease related to an at least partly impaired DNA repair system, comprising:

providing at least one cell of an individual suffering from, or at risk of suffering from, the disease with a nucleic acid molecule encoding HR23 protein and/or an HR23 protein-binding molecule, or a functional part, derivative and/or analogue thereof. Preferably, the HR23 protein-binding molecule comprises XPC, MAG, CREB, p53, or a functional part, derivative and/or analogue thereof. More preferably, the DNA repair system comprises a global genome nucleotide excision repair system and/or base excision repair system.

Multiple engagements between HR23 and cell cycle regulation are apparent. Since HR23 is capable of binding to primary damage sensors such as XPC and MAG, HR23 can be used to influence coordinated control of major cellular DNA damage response pathways, including DNA repair, cell cycle progression and checkpoints, apoptosis and chromosome segregation. In one aspect, the invention therefore provides a use of an HR23 protein, or a functional part, derivative and/or analogue thereof, for influencing apoptosis, cell cycle control and/or chromosome segregation in a eukaryotic cell. Such assays are very relevant for testing the action of novel therapeutic agents for their mutagenic and/or cytotoxic properties, and for detection of side effects of specific treatments and/or medication.

The invention is further explained in the following examples. The examples only serve to clarify the invention and do not limit the scope of the invention in any way.

EXAMPLES

Experimental Procedures

Construction of mHR23A Targeting Vector

An Ola129 mHR23A targeting construct was generated by converting the BglII site in exon II of clone pG7M23Ag1 (containing a 4 kb genomic EcoRI fragment subcloned in pGEM7) into a ClaI site, which (due to a ClaI site in the polylinker) allowed deletion of sequences downstream of the BglII site in exon II (clone pG7M23Ag7). Next, the remaining EcoRI site was removed by filling in the overhangs with Klenow, resulting in clone pG7M23Ag9. After changing the BstXI site into an SalI site, the 3 kb XhoI-SalI fragment was cloned into SalI-digested pGEM5, resulting in clone pG5M23Ag17. Next, the 3' arm of the construct, consisting of a Klenow-blunted 1.5 kb SmaI-XbaI fragment starting at the SmaI site in exon VII, was inserted in the blunted NdeI site of pG5M23Ag17 (giving pG5M23Ag20), followed by insertion of a Neo marker cassette in antisense orientation in the ClaI site (giving pG5M23Ag24). Finally, the NotI-NsiI insert of pG5M23Ag24 was recloned into a pGEM-9Zf(−) based vector containing a 2.8 kb thymidine kinase (TK) marker cassette (giving pG5M23Ag30).

ES Cell Culture and Transfection

The Ola129-derived ES cell line E14 was electroporated with the mHR23A targeting construct and cultured on dishes treated with gelatin as described previously (Ng et al., 2002). G418 (GENETICIN®, Gibco, final concentration 200 µg/ml) was added 24 hr after electroporation and cells were maintained under selection for 6-8 days. Genomic DNA from G418-resistant clones was digested with BamHI and subjected to Southern blot analysis using a 0.6 kb XbaI-RsaI fragment (3' external to the construct) as a probe. Targeted clones were subsequently screened with a Neo cDNA probe (ClaI fragment) to confirm proper homologous recombination in the 5' arm.

Generation of the mHR23A$^{-/-}$ and mHR23A$^{-/-}$/B$^{-/-}$ (DKO) Mice and Fibroblasts Cells from two independent targeted clones with 40 chromosomes were injected into 3.5-day-old blastocysts isolated from pregnant C57BL/6 females (Ng et al., 2002). Male chimeric mice were mated with C57BL/6 females to obtain heterozygous animals. Germ line transmission was observed in the coat color of F1 offspring. Heterozygous males and females for mHR23A were interbred to generate mHR23A$^{+/+}$, mHR23A$^{+/-}$, and mHR23A$^{-/-}$ mice. For the generation of double mutant mHR23A/B mice, male and female animals heterozygous for both mHR23A and mHR23B (Ng et al., 2002) were interbred. Genotyping was performed by Southern blot or PCR analysis of genomic DNA from tail biopsies of 10-14 day old pups.

Primary mHR23A MEFs (three independent lines per genotype) were isolated from day 13.5 embryos (E13.5) obtained from matings between mHR23A$^{+/-}$ mice. Double mutant mHR23A/B MEFs were isolated from day 8.5 embryos (E8.5) derived from different crossings between mHR23A$^{+/-}$/B$^{+/-}$ and mHR23A$^{-/-}$/B$^{+/-}$ mice. Part of the embryo was used for genotyping and the remaining tissue was minced and immersed in a thin layer of F10/DMEM culture medium (Gibco BRL) supplemented with 15% fetal calf serum, 2 mM glutamate, and 50 µg/ml penicillin and streptomycin. Spontaneously immortalized (established) cell lines were obtained by continuous subculturing of primary MEFs.

For the genotyping of E8.5 embryos, the yolk sac was used as described (Gurtner et al., 1995). In short, the yolk sac was collected in 20 µl of water and immediately frozen in dry ice. Samples were heated for 5 min at 95° C. and incubated with 1 µl of proteinase K (10 mg/ml) for 1 hr at 55° C. Proteinase K was heat-inactivated for 5 min at 95° C. PCR analysis was performed using the three primer sets described below for 30 cycles (93° C., 1 min; 55° C., 1 min; 72° C., 90 sec) using mHR23A and mHR23B primers.

Primer set 1: mHR23Ap1 (5'-atg-gga-ctt-ggg-cat-agg-tga-3') (SEQ ID NO:1), mHR23Ap2 (5'-tct-tca-gcc-agg-cct-ctt-ac-3') (SEQ ID NO:2) and anti-sense neo (5'-atc-tgc-gtg-ttc-gaa-ttc-gcc-aat-g-3') (SEQ ID NO:3) giving 243 and 350 by PCR fragments from the wild-type and targeted allele, respectively. Primer set 2: mHR23Bp1 (5'-gta-aag-gca-ttg-aaa-gag-aag-3') (SEQ ID NO:4), mHR23Bp2 (5'-cta-cag-tct-tgt-ttc-tga-cag-3') (SEQ ID NO:5) and anti-sense pgk3 (5'-tag-ggg-agg-agt-aga-agg-tg-3') (SEQ ID NO:6) giving 202 and 600 bp PCR fragments from the wild-type and targeted allele, respectively.

DNA Repair Assays and Microneedle Injection

UV sensitivity was determined as described (Ng et al., 2002). MEFs cultures were exposed to different doses of UV-C light (254 nm, Philips TUV lamp) and allowed to grow for another 3-5 days before reaching confluence. The number of proliferating cells was estimated by scintillation counting of the radioactivity incorporated during a 3 hr pulse with [$^3$H]thymidine (5 µCi/ml, specific activity (s.a.): 50 Ci/mmole; Amersham). Cell survival was expressed as the ratio of $^3$H incorporation in irradiated and non-irradiated cells.

UV-induced global genome repair was assayed using the UDS method as described (Vermeulen et al., 1994). Cells were exposed to 16 J/m$^2$ of 254 nm UV light and labeled with [methyl-3H]thymidine (10 µCi/ml, s.a.: 50 Ci/mmole). Repair capacity was quantified by grain counting after autoradiography.

RNA synthesis recovery after UV irradiation was measured according to Ng et al. (2002). Cells were exposed to 10 $J/m^2$ of 254 nm UV light, allowed to recover for 16 hr, labeled with [5,6-3H]uridine (10 µCi/ml, s.a.: 50 Ci/mmole), and processed for autoradiography. The relative rate of RNA synthesis was expressed as the number of autoradiographic grains over the UV-exposed nuclei divided by the number of grains over the nuclei of non-irradiated cells on parallel slides.

Microneedle injection of control cells (C5RO) was performed as described previously (Vermeulen et al., 1994). After injection of at least 50 homopolykaryons, cells were cultured for the desired time in normal culture medium before they were assayed for their repair capacity by means of UV-induced UDS.

RNA and Protein Analysis

Total RNA was isolated from mHR23A MEFs using an RNEASY® Mini Kit (Qiagen). 20 µg of total RNA was separated on a 0.9% agarose gel and transferred to HYBOND®-N+ membrane (Amersham Pharmacia Biotech). RNA blots were hybridized using mHR23A and β-actin $^{32}$P-labeled cDNA probes.

Immunoblot analysis was performed on fibroblast extracts obtained by sonification ($5 \times 10^6$ cells in 300 µl phosphate-buffered saline (PBS)) or extraction. In the latter case, NP lysis buffer (25 mM Tris-HCl (pH 8.0), 1 mM EDTA, 10% glycerol, 0.01% Nonidet P-40, 1 mM dithiothreitol, 0.25 mM phenylmethylsulfonyl fluoride, and protease inhibitor mix (chymostatin, leupeptin, antipain, and pepstatin A)) was added to a monolayer of MEFs. After 30 minutes on ice, the lysate was collected with a cell scraper and clarified by 2 times centrifugation at 4° C. NP lysis buffer containing 0.3 M NaCl was added to the cell pellet and homogenized by sonification.

SDS polyacrylamide gel electrophoresis was performed by loading 25-50 µg of total cellular protein per lane on 6-8% gels. Proteins were blotted to nitrocellulose membranes (Schleicher & Schuell) and probed with polyclonal antibodies recognizing human HR23A or XPC, or with monoclonal antibodies recognizing the HA epitope (HA.11, BAbCO) or p62 subunit of TFIIH (C39, kindly provided by Dr. J. M. Egly). Proteins were visualized using alkaline phosphatase-labeled goat anti-rabbit or peroxidase-conjugated goat anti-rabbit or goat anti-mouse secondary antibodies.

Immunofluorescence Labeling

Cells were grown on glass coverslips at 60-80% confluency. After washing twice with PBS, cells were fixed with 2% paraformaldehyde in PBS for 10 min at room temperature (RT) and permeabilized with 0.1% Triton X-100 in PBS for 2× 10 min at RT. After extensive washing (three times of 5 min each) with PBS$^+$ (PBS supplemented with 0.15% glycine and 0.5% BSA), cells were incubated with affinity-purified primary antibodies in PBS$^+$ in a moist chamber for 1½ hr at RT. After washing five times in PBS$^+$, cells were incubated with the secondary antibodies for 1½ hr in PBS$^+$ in a moist chamber at RT. Following 5 washes with PBS$^+$ and once with PBS, coverslips were preserved with VECTASHIELD® Mounting Medium (Vector Laboratories) containing 4'-6-diamidino-2-phenylindole (DAPI, 1.5 µg/µl) to visualize the nuclei.

Primary antibodies used: affinity-purified, rabbit polyclonal anti-human XPC; rabbit polyclonal anti-human ERCC1; rabbit polyclonal anti-XPA (a kind gift from Dr. K. Tanaka); mouse monoclonal anti-p62 of TFIIH subunit (3C9, J. M. Egly, Illkirch); and high affinity, rat monoclonal anti-HA (3F10, Boehringer). Secondary antibodies were: goat anti-rat and goat anti-rabbit Alexa 594-conjugated, and goat anti-rat and goat anti-rabbit Alexa 488-conjugated antibodies (Molecular probes); and goat anti-mouse Cy3-conjugated antibodies (Jackson ImmunoResearch Laboratories).

Generation of XPC-GFP Fusion cDNA Construct and Cotransfection Studies

Full-length human XPC cDNA (ScaI-Asp718I fragment) was cloned in EcoRI-Asp718I digested eukaryotic expression vector pEGFP-N3 (Clontech) containing a 3' histidine-hemagglutinin tag (generated by insertion of a double-stranded oligonucleotide in SspBI-NotI digested pEGFP-N3; kindly provided by D. Hoogstraten). For simplicity, the resulting tagged cDNA construct hXPC-EGFP-His$_6$HA-N$_3$ is referred to as hXPC-GFP.

Full-length cDNAs of the hHR23B (in a pSLM vector, Pharmacia Biotech) and hXPC-GFP were cotransfected into DKO MEFs using puromycin as a selectable marker. The transfection was performed using SUPERFECT® Transfection Reagent (Qiagen) and puromycin was added 24 hr after transfection to a final concentration of 1 µg/ml, and the cells were maintained under selection for 20-40 days. Stable puromycin-resistant clones were isolated and integration of the cDNA construct was confirmed by DNA blotting (data not shown).

Exposure of Cells to DNA Damaging Agents

Cells stably expressing hXPC-GFP/hHR23B were rinsed with PBS, exposed to UV-C light (254 nm; Philips TUV lamp, dose as indicated in the text) and subsequently cultured at 37° C. for various time periods (as indicated in the text). XPC was detected either by immunoblot analysis or by visualization in living cells using fluorescence microscopy. A similar approach was used to study the effect of N-acetoxy-2-acetylaminofluorene (NA-AAF, final concentration 50 or 100 µM), mitomycin C (MMC, Sigma, final concentration 1.2 or 2.4 µg/ml), ionizing radiation (γ-rays from a $^{137}$Cs source, single dose of 6 and 10 Gy), the proteasome inhibitor N-CBZ-LEU-LEU-LEU-AL (CBZ-LLL, Sigma, final concentration 5 or 10 µM), the transcription inhibitor 5,6-dichloro-1β-D-ribofuranosyl-benzimidazole (DRB, Sigma, final concentration of 100 µM, 2-3 hrs), the translation inhibitor cyclohexamide (CHX, Boehringer, final concentration 30, 50, and 100 µg/ml, 1-3 hours), heat shock (39.5 and 41° C., for 2-12 hrs), and the nuclear export inhibitor leptomycin B (LMB, Sigma, final concentration 10 ng/ml).

Local UV irradiation was obtained by covering cells grown on glass coverslips with an isopore polycarbonate filter with pores of 5.0 µm diameter (Millipore, TMTP) during UV irradiation (4×16 $J/m^2$ UV-C). Immediately after exposure, the filter was removed and medium was added back to the cells and culturing was continued. After various time periods (as indicated in the text), cells were processed for immunolabeling.

To identify cells in mixtures of control and mutant fibroblasts, cells were labeled with latex beads (diameter 0.79 µm, POLYBEAD® Carboxylate Microspheres, Polysciences) added to fibroblasts cultures 2 days prior to mixing of the cells. Cells were thoroughly washed in PBS (3×) before trypsinization to remove the non-incorporated beads and seeded in a 1:1 ratio on coverslips and cultured for 2 days.

Heterokaryon Nuclear-Cytoplasmic Shuttling Assay

The shuttling assay using heterokaryons was performed as described (Borer et al., 1989). One day before cell fusion, DKO cells stably expressing hXCPC-GFP/hHR23B and HeLa cells were seeded in a 1:1 ratio on coverslips. Six hours prior to fusion, cells were irradiated with 10 $J/m^2$ UV-C or treated with 10 µM CBZ-LLL. Cell-fusion was induced (after washing with PBS) by treatment with 50% polyethylene glycol 6,000 in HANKS™ (Gibco) for 2 min followed by (3×)

washing with PBS. Finally, cells were cultured in fresh medium either supplemented with or without leptomycin B (LMB, final concentration 10 ng/ml). Three to five hours after fusion, cells were fixed with 2% paraformaldehyde and immunostained with rat monoclonal anti-HA (to monitor the XPC-GFP-His$_6$HA protein) and rabbit polyclonal anti-human ERCC1 (to distinguish human nuclei from mouse nuclei, since it specifically recognizes human ERCC1) and subsequently with appropriate secondary antibodies (see above).

Light Microscopy and Image Analysis

Immunofluorescent microscopy images were obtained with either a Leitz Aristoplan microscope equipped with epifluorescene optics and a PlanApo 63×/1.40 oil immersion lens or a Leica DMRBE microscope equipped with epifluorescene optics and a PL Fluotar 100×/1.30 oil immersion lens. For the detection of GFP-tagged proteins in the living cell, an Olympus IX70 microscope equipped with epifluorescence optics and Olympus PlanApo 60×/1.40 oil immersion lens was used. GFP images were obtained after excitation with 455-490 and long pass emission filter (>510 nm). Cy-3 images were obtained after excitation with 515-560 and long pass emission filter (580 nm).

Results

Generation of mHR23A-Deficient Mice and Cells

To generate a mouse model for mHR23A, a targeting construct was used in which exons III to VI and part of exons II and VII (encoding residues 55 to 288 of the mHR23A protein) were replaced by the neomycin resistance marker. Gene targeting creates an mHR23A allele encoding a severely truncated protein in which >85% of the coding sequence is deleted (even truncating the UbL domain) and thus can be considered a null-allele (FIG. 1A). Two correctly targeted clones (obtained at a frequency of 16%, FIG. 1B) were used for blastocyst injections. Heterozygous offspring from matings between germ line chimeric males and C57BL/6 female mice was intercrossed to generate homozygous mutant mHR23A animals (FIG. 1C), as well as day 13.5 embryos (E13.5) for isolation of mouse embryonic fibroblasts (MEFs). Neither the mHR23A mRNA nor the 50 kDa mHR23A protein could be detected in mHR23A$^{-/-}$ MEFs (FIGS. 1D and 1E). The two independent mouse lines were biochemically and phenotypically indistinguishable for all parameters tested.

mHR23A$^{-/-}$ Animals and MEFs are NER Proficient

Figure 2:
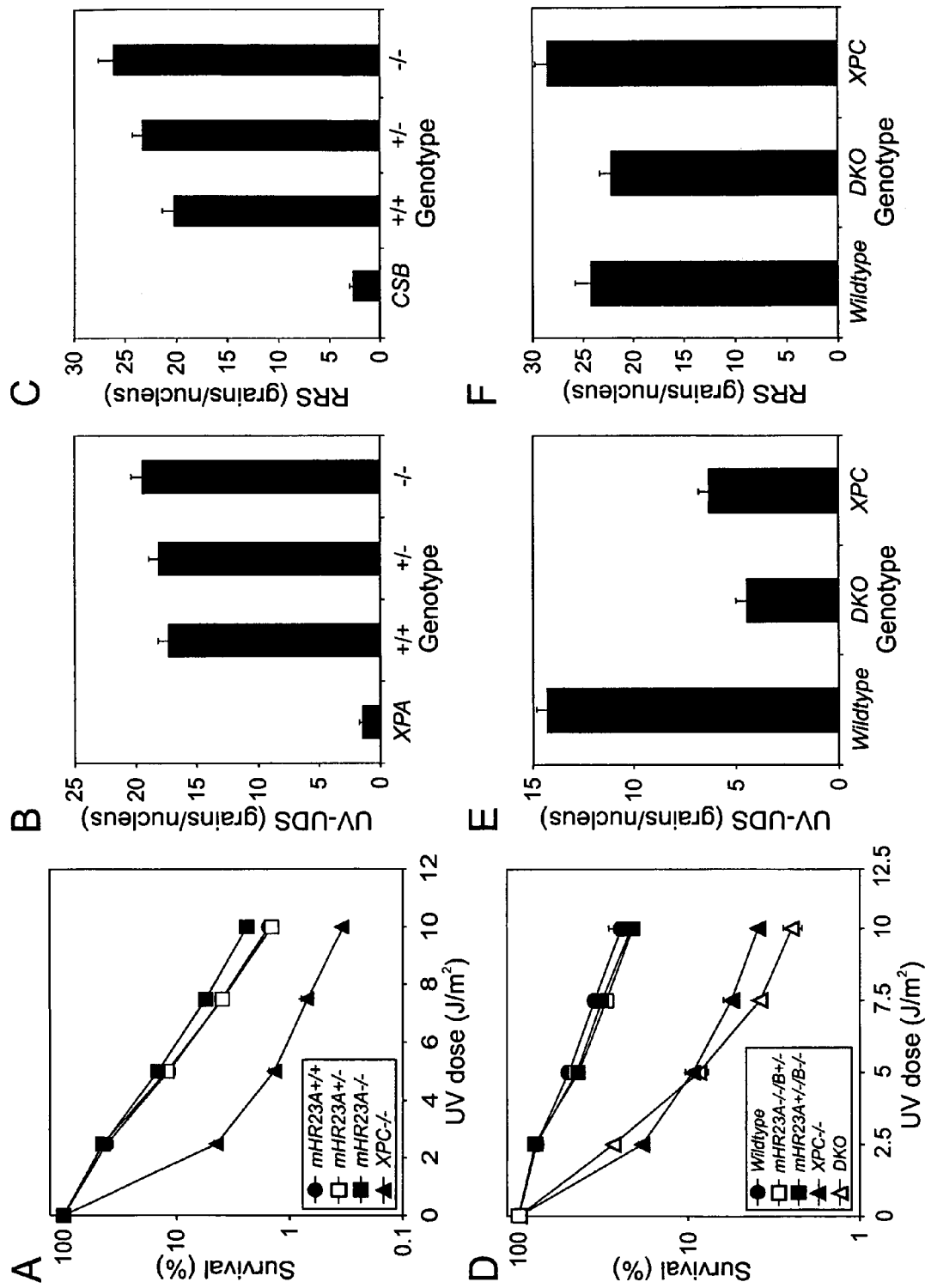

We assessed key repair parameters in mHR23A$^{-/-}$ MEFs. As shown in FIGS. 2A-2C, UV survival, UV-induced unscheduled DNA synthesis (UDS), and RNA synthesis recovery after UV exposure were all in the wild-type range, indicating that global as well as transcription-coupled NER are unaffected, mimicking the situation in an mHR23B mutant (Ng et al., 2002). These data show that mHR23A and mHR23B are functionally redundant for NER in vivo.

In striking contrast to mHR23B$^{-/-}$ animals, mHR23A$^{-/-}$ were born with Mendelian frequency and appeared indistinguishable from wild-type and heterozygous littermates for all parameters tested (including morphology, main pathology, and growth rate up to 16 months). mHR23A$^{-/-}$ male and female mice were fertile, and their mating activity and litter size were normal. Apparently, mHR23A is not essential for mouse development and mHR23B can compensate for any additional functions of mHR23A.

Total mHR23 Deficiency is Incompatible with Animal Life

In order to investigate the effect of a total mHR23 deficiency, mHR23A$^{-/-}$/B$^{-/-}$ animals (hereafter referred to as "DKO" for double knockout) were tried to be generated and to obtain corresponding MEFs by double heterozygous matings. Remarkably, out of 427 newborns analyzed, no DKOs were found (Table 1). This shows that inactivation of mHR23A aggravates the severe developmental defects caused by an mHR23B deficiency (Ng et al., 2002) to a level incompatible with life. Whereas phenotypically normal mHR23A$^{-/-}$/B$^{+/-}$ mutant mice at Mendelian ratios (71/427 found and 83/427 expected) were obtained, surprisingly mHR23A$^{+/-}$/B$^{-/-}$ animals were not born (0/427). However, isolate E13.5 mHR23A$^{+/-}$/B$^{-/-}$ mutant MEFs were isolated although they showed poor growth. Apparently, loss of even one allele of mHR23A in a complete mHR23B null-background causes lethality in embryogenesis.

To investigate embryonic lethality caused by a complete mHR23B deficiency, embryos at various stages of development were isolated. No DKO embryos were present at days 13.5 and 10.5, but growth-retarded mHR23-deficient embryos were observed at day 8.5. Importantly, three DKO MEF lines were isolated from E8.5 embryos (3/43, see Table 1). Compared to wild-type and double heterozygous mutant MEFs, these cells displayed reduced rates of proliferation, which resulted in the loss of two lines. Nevertheless, one DKO cell line was established after 30 weeks culturing, which permitted functional characterization of a total mHR23B deficiency.

Total mHR23-Deficient Cells Show an XPC-Like Repair Phenotype

Cell survival experiments revealed that DKO MEFs are remarkably similar to the unique NER phenotype of XPC$^{-/-}$ cells in terms of UV survival (FIG. 2D), deficiency of UV-induced UDS and proficiency of RNA synthesis recovery after UV exposure (FIGS. 2E and F). In contrast, MEFs retaining only one mHR23A or mHR23B allele were NER competent (FIG. 2D). Apparently, one out of four mHR23 copies is sufficient for normal NER activity.

We have examined the status of the XPC protein in the DKO MEFs. Interestingly, steady-state levels of XPC appeared strongly reduced in DKO MEFs compared to wild-type and mHR23A$^{-/-}$ cells (FIG. 1E), as shown by comparative immunofluorescence (FIG. 3A) and immunoblot analysis of cell extracts (FIG. 3B). Thus, in the absence of both mouse RAD23 proteins, XPC is unstable.

hHR23B and hXPC-GFP Rescue the UV Sensitivity of DKO Cells

To provide direct evidence that the XPC-like phenotype of DKO cells is specifically caused by the mHR23 defect, (human) hHR23B cDNA into DKO MEFs were stably transfected. The UV sensitivity of DKO cells hHR23B was only partly rescued, perhaps due to human-mouse differences (FIG. 4A). Importantly, expression of hHR23B induced an increase in the total amount of endogenous (mouse) mXPC, as shown by both immunoblot (FIG. 4C, lane 4) and immunofluorescence analysis (FIG. 4D).

Subsequently, double mutant MEFs that stably express (human) hXPC were generated, tagged with GFP (and additional His6 (SEQ ID NO:21) and HA tags)) (FIG. 4B), to allow direct observation in living cells. Functionality of the hXPC-GFP was demonstrated after microinjection and transfection of the cDNA construct in XPC-deficient cells (data not shown). Although hXPC-GFP was undetectable by fluorescence microscopy (FIG. 4E), stable transformants (verified for the presence of hXPC-GFP cDNA by DNA blotting) had largely regained wild-type UV resistance (FIG. 4A), indicating that the repair defect was rescued. Introduction of hXPC-GFP appeared to restore endogenous mXPC levels as shown by immunoblot (FIG. 4C, lane 5) and immunofluorescence analysis (not shown). Apparently, hXPC-GFP has a trans-effect on mXPC stability.

To investigate the stabilizing effect of mHR23B on XPC, hHR23B with hXPC-GFP cDNA was cotransfected into DKO cells. Stably transfected clones exhibited wild-type UV resistance (FIG. 4A) and normalized levels of endogenous mXPC (FIG. 4C, lane 6, and not shown). In contrast to MEFs expressing only hXPC-GFP, a small fraction (<10%) of the double cotransfected cells displayed green fluorescent nuclei (FIG. 4F). This is due to a level of hXPC-GFP expression below the detection limit since immunofluorescence using anti-HA monoclonals revealed that the majority of the cells expressed the tagged transgene (data not shown). These data show that the cotransfected hHR23B acts as a stabilizing factor for both hXPC-GFP and endogenous mXPC.

DNA Damage Causes Accumulation of hXPC-GFP

Figure 5:
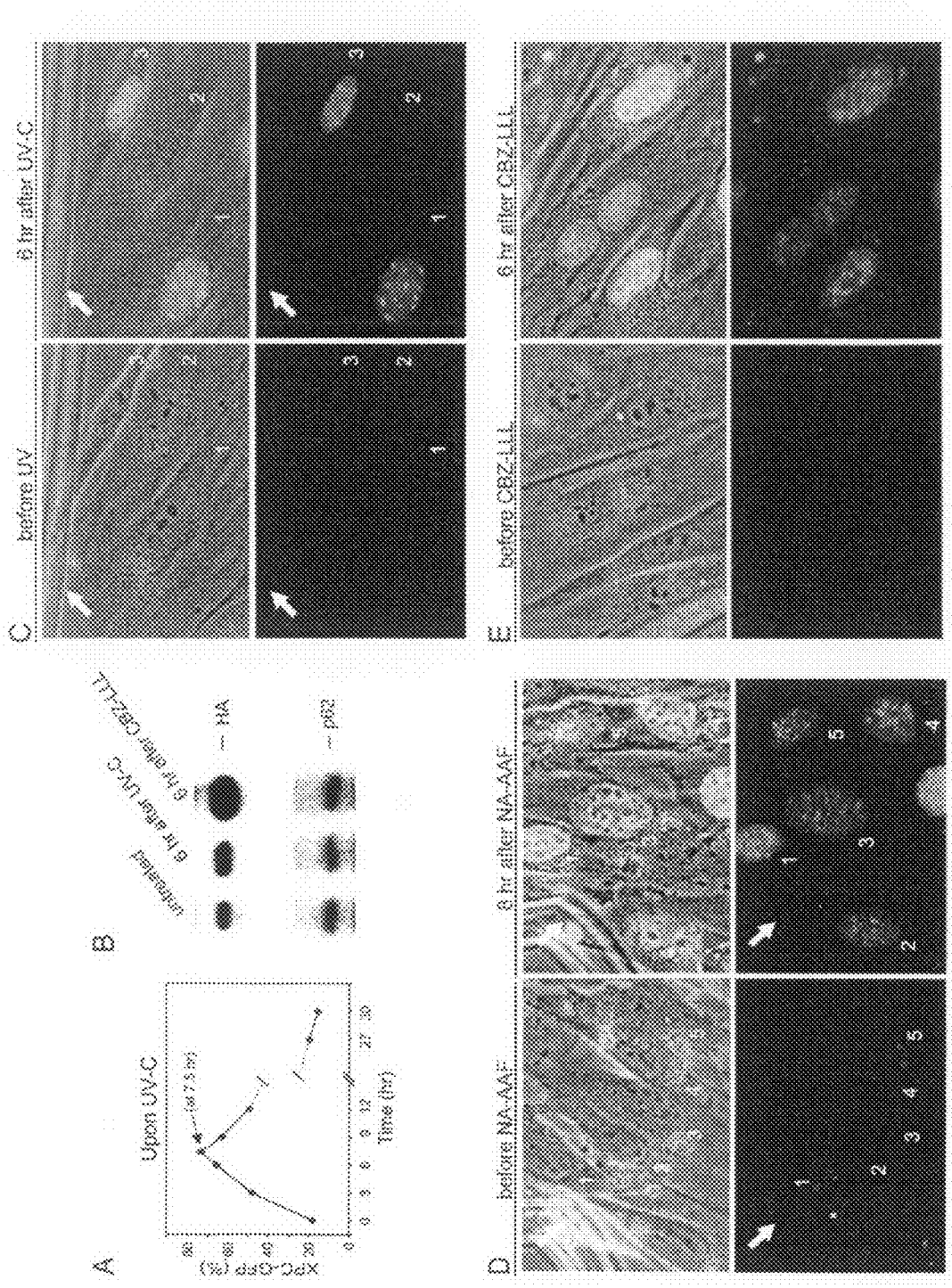

The hXPC-GFP/hHR23B DKO cell line provided a convenient tool to monitor the effect of DNA damage on the XPC steady-state level and mobility in living cells. Interestingly, UV irradiation (5 and 10 $J/m^2$) strongly increased the percentage of green cells and the intensity of the GFP signal. Kinetic analysis upon UV exposure revealed a time-dependent reversible accumulation of XPC-GFP in the majority of the cells (FIG. 5A); this was further illustrated by monitoring individual cells in time after UV irradiation (FIG. 5C). In addition, these findings were corroborated by immunoblotting of whole cell extracts using antibodies against the HA epitope attached to the GFP tag (FIG. 5B, lane 2) and anti-HA immunocytochemistry (not shown). Since this phenomenon was specific for DKO cells transfected with hXPC-GFP/hHR23B, these results show that XPC levels are responsive to UV in an HR23-dependent fashion.

To investigate whether XPC accumulation is specific for NER-type DNA damage or just stress-related, cells were exposed to different kinds of genotoxic agents. N-acetoxy-2-acetylaminofluorene (NA-AAF, 50 and 100 µM), which induces bulky adducts processed by NER, elicited a very potent UV-like response in all cells within 6 to 8 hrs (FIG. 5D). In contrast, γ-rays (6 and 10 Gy) and mitomycin C (MMC, 1.2 and 2.4 µg/ml), inducing mainly strand breaks and interstrand cross-links respectively (which are dealt with by other repair pathways), failed to provoke detectable XPC accumulation. Also heat shock (41° C., analyzed for up to 12 hrs) failed to boost fluorescence. The possibility that UV and NA-AAF evoked a general accumulation of protein was ruled out since cells expressing GFP alone do not exhibit a significant increase in fluorescence after genotoxic insults. This shows that lesions specifically recognized by the NER pathway enhance the level of HR23-dependent hXPC-GFP.

One of the direct consequences of UV- and NA-AAF-induced DNA damage is a temporary block of transcription. To investigate whether hXPC-GFP accumulation requires transcription or is induced by a DNA damage independent blockage of transcription, mRNA synthesis in DKO cells expressing hXPC-GFP/hHR23B was reversibly arrested by incubation with 5,6-dichloro-1β-D-ribofuranosyl-benzimidazole (DRB, 100 µM). No induction of XPC-GFP fluorescence was observed: instead, preincubation with DRB (2-3 hrs) prior to UV treatment prevented UV-induced XPC-GFP accumulation (data not shown). Consistent with this result, no enhanced XPC fluorescence was found in cells treated with the translational inhibitor cyclohexamide (30 and 50 µg/ml), demonstrating the requirement for de novo RNA and protein synthesis. In non-challenged conditions, the steady-state level of XPC remains low.

hXPC-GFP is Degraded Via Ubiquitin/Proteasome-Dependent Proteolysis

To further examine the HR23-dependent XPC stabilization, DKO cells expressing hXPC-GFP/hHR23B were incubated with the proteasomal proteolysis inhibitor N-CBZ-LEU-LEU-LEU-AL (CBZ-LLL, 5 and 10 µM) (Wiertz et al., 1996). Similar to UV irradiation and NA-AAF, all cells displayed a striking XPC-GFP accumulation in time (FIG. 5E), which was reversible upon drug removal (not shown). Both immunoblot analysis (FIG. 5B, lane 3) and immunocytochemistry using anti-HA antibodies (not shown) confirmed the above observations. These findings show that degradation of XPC-GFP occurs via ubiquitin/proteasome-dependent proteolysis and that an agent capable of at least in part inhibiting proteolysis can be detected by determining whether XPC accumulates in a cell.

Application of Local UV Damage to hXPC-GFP Expressing Cells

To explore the mechanism by which hXPC-GFP is stabilized, a recently developed method for induction of DNA damage in a restricted part of the nucleus was employed. For this purpose, a monolayer of DKO cells expressing hXPC-GFP/hHR23B was covered with a UV light-shielding isopore polycarbonate filter (pore diameter ~5 µm). Upon UV irradiation, only at the position of pores is UV damage induced, as detected with antibodies that specifically recognize CPD and 6-4PP lesions. These locations attract all NER proteins tested thus far. Cells were fixed at different time points after UV irradiation to allow simultaneous immunostaining with antibodies against various proteins and GFP fluorescence microscopy (FIGS. 6A, 6B). Non-irradiated nuclei and non-damaged regions within partly irradiated nuclei serve as internal controls. Very rapidly (<2 minutes) after UV exposure, GFP fluorescence and anti-HA immunostaining revealed high local accrual of hXPC-GFP($His_6$HA) in part of the nuclei, which colocalized with XPA (FIG. 6A) and the p62 subunit of TFIIH (not shown). These findings demonstrate that, in living cells, the GFP-tagged XPC protein translocates very rapidly to sites containing UV lesions.

If XPC stabilization only occurs when bound to the damage, an increase in fluorescent signal selectively at the damaged sites would be expected. On the other hand, with an (additional) overall stabilization of hXPC, it is expected that, in time, a concomitant increase of fluorescence over the entire nucleus (in addition to the damaged area) will be observed in comparison to non-damaged nuclei. The increase of hXPC-GFP (FIG. 6A) initially occurs only at the locally damaged sites, but after two hours also in the remainder of locally damaged nuclei, a clearly higher signal is noted when compared to non-exposed nuclei in the vicinity (FIG. 6B). These findings demonstrate an overall intranuclear stabilization of hXPC-GFP triggered by binding to lesions.

High Levels of XPC Mediate a Transient Enhancement of DNA Repair

To investigate the biological consequence of DNA damage-induced stabilization of XPC, the DNA repair capacity (UV-induced UDS) in DKO cells expressing XPC-GFP/hHR23B prechallenged with UV light. Five hours post UV irradiation (10 $J/m^2$) were tested the mean UDS level (as determined by 1 hr $^3$H-thymidine pulse-labeling immediately after a dose of 16 $J/m^2$) was 1.5-fold increased compared to cells assayed in parallel that were not pre-irradiated (FIG. 7A). UV-induced XPC-GFP accumulation was confirmed microscopically (data not shown) just prior to the UDS assay. The increase in UDS is not derived from the additional effect of NER still dealing with lesions remaining of the first UV dose, since in a separate UDS experiment without the second UV irradiation, no significant UDS was observed (not shown). These data demonstrate that UV-induced accumulation of XPC-GFP causes a concomitant increase in GG-NER. Enhanced repair by increased levels of XPC was confirmed by microinjection of XPC-GFP cDNA into homopolykaryons of wild-type human fibroblasts. Microinjected cells expressing XPC-GFP (FIG. 7A, top right panel) exhibit a higher UDS compared to neighboring, non-injected monokaryons (FIG. 7B). In contrast, when a cocktail of XPC-GFP and hHR23B was injected, UDS in the majority of the cells was significantly lower and injection of this cocktail appeared highly toxic (data not shown). These data demonstrate that large amounts of stabilized XPC (as a result of overexpressed hHR23B) can reduce cell viability.

Sequestration of XPC in the Nucleus Caused a Reduced Proteolysis

The findings above demonstrate that XPC levels are under tight control in an HR23-dependent fashion. Close inspection of the XPC sequence revealed several potential nuclear location (NLS) and nuclear export (NES) signals (provisionally referred to as NES1, NES2 and NES3, FIGS. 8A and B). It was therefore investigated whether nuclear-cytoplasmic shuttling regulates XPC levels as reported for several other short-lived proteins, such as p53 and clock proteins (Sionov et al., 2001; Yagita et al., 2002) and whether DNA damage influences this process.

Figure 4:
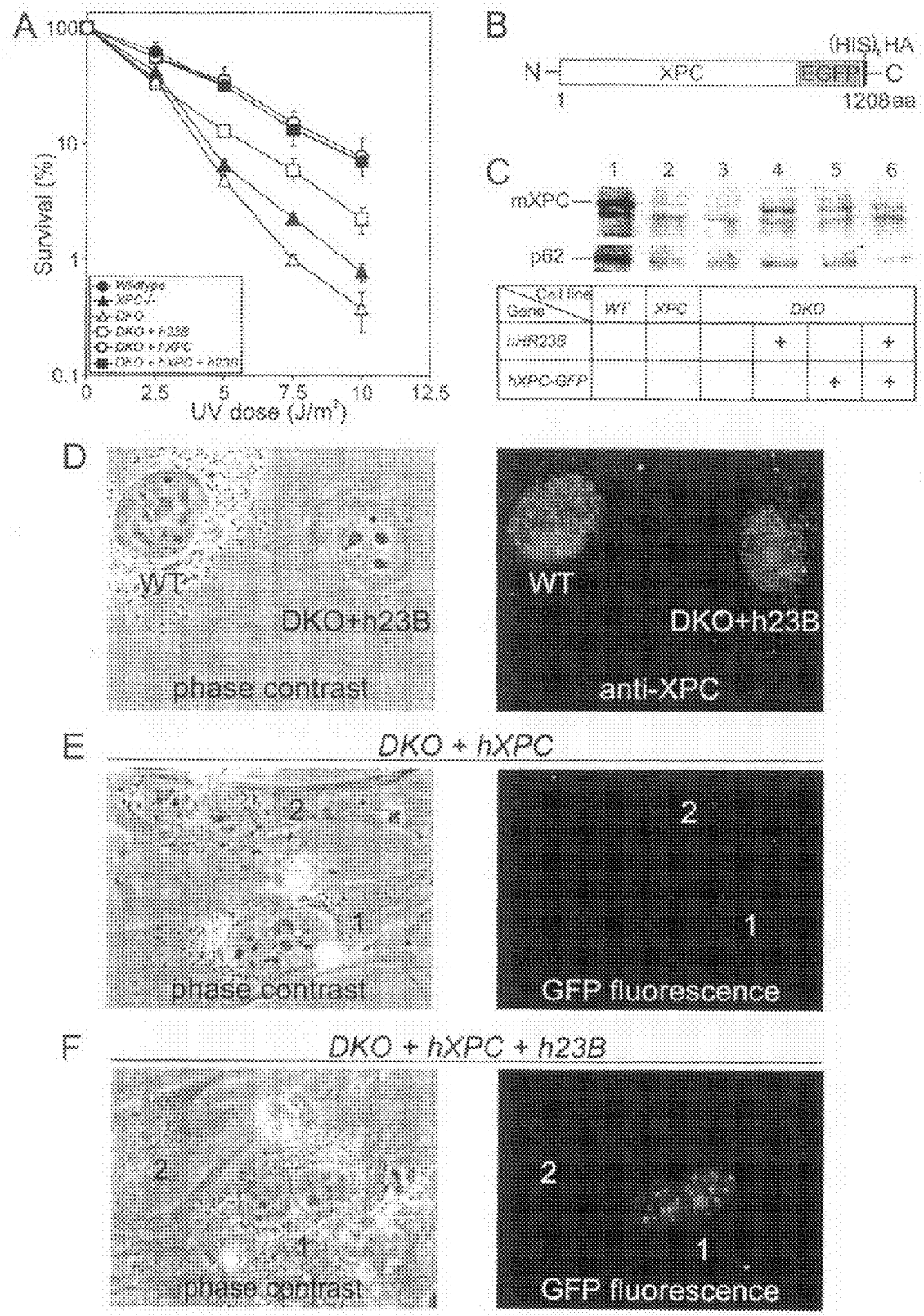
Figure 8:
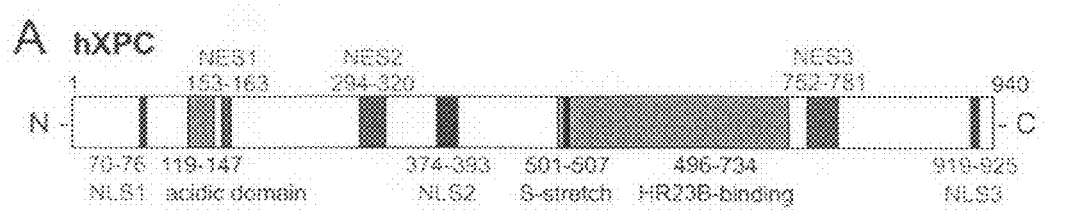
Figure 8:
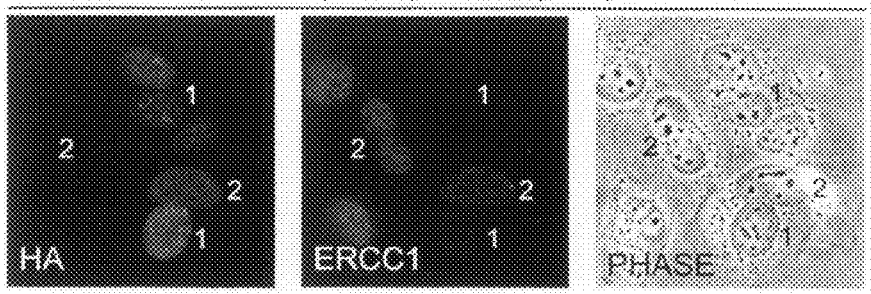
Figure 8:
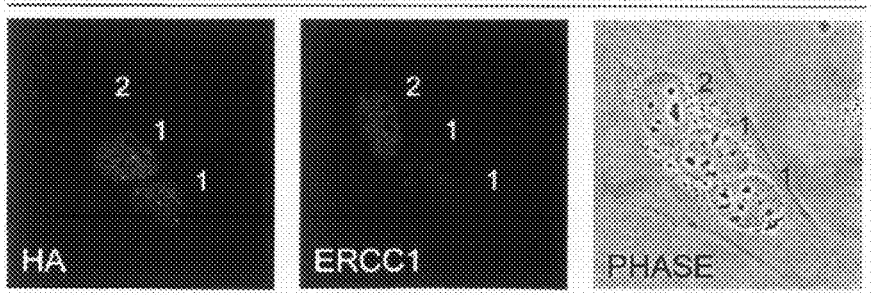

Nuclear export occurs via the chromosome region maintenance 1 (CRM1)/Exportin1 system (Mattaj and Englmeier, 1998; Nigg, 1997). To investigate whether XPC shuttles between nucleus and cytoplasm, the effect of leptomycin B (LMB), an established specific inhibitor of CRM1/Exportin1-mediated nuclear export (Formerod et al., 1997; Fukuda et al., 1997), on the location of XPC-GFP was studied. Using a heterokaryon nuclear-cytoplasmic shuttling assay (Borer et al., 1989) with DKO cells stably expressing XPC-GFP/hHR23B fused to human cells (HeLa), transport of the fluorescent protein (both in the presence and absence of 10 ng/ml LMB) from mouse nuclei to human nuclei can be monitored. Four hours after fusion, cells were immunostained with anti-HA monoclonals to identify the fusion protein (XPC-GFP-His$_6$HA) and specific human ERCC1 antibodies (that do not cross react to rodent ERCC1) to recognize HeLa nuclei. As shown in FIG. 8C, 4 hr after fusion in the absence of LMB, the nuclear pool of XPC-GFP induced by 10 J/m$^2$ UV-C light (given 6 hr prior to cell fusion) in the DKO cells was exchanged with non-irradiated human nuclei. Administration of LMB directly after cell fusion prevented this exchange (FIG. 8D), showing that export from the mouse nuclei was responsible for the accumulation of the XPC-GFP in the untreated HeLa nuclei. A similar effect on the XPC-GFP shuttling was observed when XPC-GFP accumulation was provoked by 10 µM CBZ-LLL treatment (not shown). Parallel to the documented cases of p53 and clock proteins these findings demonstrate that proteolysis of XPC involves a nuclear-cytoplasmic shuttling mechanism.

Generation of Clones Provided with Murine HR23

The mHR23A/mHR23B double mutant cells are transfected with complementing functional mHR23A or mHR23B cDNAs tagged with versions of the GFP fluorescent marker to permit in vivo dynamic studies. Additionally, the mouse HR23 cDNA's are provided with other tags facilitating purification on the basis of affinity chromatography. Because murine genes are used in this experiment, full functional complementation is obtained, avoiding possible interspecies differences and consequent incomplete or aberrant correction of a primary defect. In some of the transfections, other genes/cDNAs known to be binding partners of HR23A or HR23B, such as XPC, MAG, p53, centrin tagged with compatible fluorescent markers and affinity tags are included in the transfection. Clones selected for stable expression of the co-transfected dominant selectable marker are screened for functional complementation of an HR23 defect and for proper expression of the other co-transfected gene. Clones are used for identifying the network regulated by the HR23 pathway and application for readout of genotoxicity and for general cellular stress.

A unifying model for the findings on HR23, XPC and proteolysis is depicted in FIG. 9. As the main initiator of GG-NER, XPC constitutes an ideal focal point for the regulation of the entire pathway, which involves HR23. Absence of HR23 proteins reveals that XPC on its own is highly unstable due to proteolysis via the 26S proteasome. Under normal conditions, HR23 complex formation with XPC results in a significant reduction of XPC proteolysis and consequently in increased steady-state levels of the protein complex. This correlates with proficient GG-NER. Under conditions of a high level of DNA damage, involvement in NER stimulates the protective role of HR23. Particularly after prolonged higher damage load, this leads to gradual up-regulation of XPC and consequently the entire GG-NER pathway. This rheostat model for adapting XPC levels to the amount of damage provides a novel type of regulation of DNA repair capacity in eukaryotes.

TABLE 1

Genotype analysis of DKO (mHR23A$^{-/-}$/B$^{-/-}$) embryos and offspring

| Stage | Analyzed | Expected* (if Mendelian) | Found |
|---|---|---|---|
| E8.5 | 43 | 7 | 3# |
| E10.5 | 14 | 1.8 | 0 |
| E13.5 | 77 | 9.1 | 0 |
| Newborn | 427 | 41.4 | 0 |

*Derived from different mHR23A$^{+/-}$/B$^{+/-}$ and mHR23A$^{-/-}$/B$^{+/-}$ intercrosses
One cell line established

REFERENCES

Araki, M., Masutani, C., Takemura, M., Uchida, A., Sugasawa, K., Kondoh, J., Ohkuma, Y., and Hanaoka, F. (2001). Centrosome protein centrin 2/caltractin 1 is part of the xeroderma pigmentosum group C complex that initiates global genome nucleotide excision repair. J Biol Chem 18665-18672, 27.

Bertolaet, B. L., Clarke, D. J., Wolff, M., Watson, M. H., Henze, M., Divita, G., and Reed, S. I. (2001). UBA domains of DNA damage-inducible proteins interact with ubiquitin. Nat Struct Biol 8, 417-422.

Biggins, S., Ivanovska, I., and Rose, M. D. (1996). Yeast ubiquitin-like genes are involved in duplication of the microtubule organizing center. J Cell Biol 133, 1331-1346.

Bootsma, D., Kraemer, K. H., Cleaver, J. E., and Hoeijmakers, J. H. J. (2001). Nucleotide excision repair syndromes: xeroderma pigmentosum, Cockayne syndrome, and trichothiodystrophy. In Scriver C R, Beaudet, A L, Sly, W S, Valle, D Vogelstein and Kinzler (eds). The Metabolic and Molecular Bases of Inherited Disease McGraw-Hill Book Co, New York 1, 677-703.

Borer, R. A., Lehner, C. F., Eppenberger, H. M., and Nigg, E. A. (1989). Major nucleolar proteins shuttle between nucleus and cytoplasm. Cell 56, 379-390.

Chen, L., and Madura, K. (2002). Rad23 promotes the targeting of proteolytic substrates to the proteasome. Mol Cell Biol 22, 4902-4913.

Chen, L., Shinde, U., Ortolan, T. G., and Madura, K. (2001). Ubiquitin-associated (UBA) domains in Rad23 bind ubiquitin and promote inhibition of multi-ubiquitin chain assembly. EMBO Rep 2, 933-938.

Clarke, D. J., Mondesert, G., Segal, M., Bertolaet, B. L., Jensen, S., Wolff, M., Henze, M., and Reed, S. I. (2001). Dosage suppressors of pds1 implicate ubiquitin-associated domains in checkpoint control. Mol Cell Biol 21, 1997-2007.

Fornerod, M., Ohno, M., Yoshida, M., and Mattaj, I. W. (1997). CRM1 is an export receptor for leucine-rich nuclear export signals. Cell 90, 1051-1060.

Friedberg, E. C., Walker, G. C., and Siede, W. (1995). DNA repair and mutagenesis. ASM Press, Washington D.C.

Fukuda, M., Asano, S., Nakamura, T., Adachi, M., Yoshida, M., Yanagida, M., and Nishida, E. (1997). CRM1 is responsible for intracellular transport mediated by the nuclear export signal. Nature 390, 308-311.

Gillette, T. G., Huang, W., Russell, S. J., Reed, S. H., Johnston, S. A., and Friedberg, E. C. (2001). The 19S complex of the proteasome regulates nucleotide excision repair in yeast. Genes Dev 15, 1528-1539.

Gurtner, G. C., Davis, V., Li, H., McCoy, M. J., Sharpe, A., and Cybulsky, M. I. (1995). Targeted disruption of the murine VCAM1 gene: essential role of VCAM-1 in chorioallantoic fusion and placentation. Genes Dev 9, 1-14.

Hanawalt, P. C. (2000). DNA repair. The bases for Cockayne syndrome. Nature 405, 415-416.

Hardeland, U., Steinacher, R., Jiricny, J., and Schar, P. (2002). Modification of the human thymine-DNA glycosylase by ubiquitin-like proteins facilitates enzymatic turnover. Embo J 21, 1456-1464.

Hiyama, H., Yokoi, M., Masutani, C., Sugasawa, K., Maekawa, T., Tanaka, K., Hoeijmakers, J. H. J., and Hanaoka, F. (1999). Interaction of hHR23 with s5a. The ubiquitin-like domain of hhr23 mediates interaction with s5a subunit of 26s proteasome. J Biol Chem 274, 28019-28025.

Hoeijmakers, J. H. J. (2001). Genome maintenance mechanisms for preventing cancer. Nature 411, 366-374.

Houtsmuller, A. B., Rademakers, S., Nigg, A. L., Hoogstraten, D., Hoeijmakers, J. H. J., and Vermeulen, W. (1999). Action of DNA repair endonuclease ERCC1/XPF in living cells. Science 284, 958-961.

Kumar, S., Talis, A. L., and Howley, P. M. (1999). Identification of HHR23A as a substrate for E6-associated protein-mediated ubiquitination. J Biol Chem 274, 18785-18792.

Lambertson, D., Chen, L., and Madura, K. (1999). Pleiotropic defects caused by loss of the proteasome-interacting factors Rad23 and Rpn10 of Saccharomyces cerevisiae. Genetics 153, 69-79.

Lombaerts, M., Goeloe, J. I., den Dulk, H., Brandsma, J. A., and Brouwer, J. (2000). Identification and characterization of the rhp23(+) DNA repair gene in Schizosaccharomyces pombe. Biochem Biophys Res Commun 268, 210-215.

Lommel, L., Chen, L., Madura, K., and Sweder, K. (2000). The 26S proteasome negatively regulates the level of overall genomic nucleotide excision repair. Nucleic Acids Res 28, 4839-4845.

Masutani, C., Araki, M., Sugasawa, K., van der Spek, P. J., Yamada, A., Uchida, A., Maekawa, T., Bootsma, D., Hoeijmakers, J. H. J., and Hanaoka, F. (1997). Identification and characterization of XPC-binding domain of hHR23B. Mol Cell Biol 17, 6915-6923.

Masutani, C., Sugasawa, K., Yanagisawa, J., Sonoyama, T., Ui, M., Enomoto, T., Takio, K., Tanaka, K., van der Spek, P. J., Bootsma, D., and et al. (1994). Purification and cloning of a nucleotide excision repair complex involving the xeroderma pigmentosum group C protein and a human homologue of yeast RAD23. Embo J 13, 1831-1843.

Mattaj, I. W., and Englmeier, L. (1998). Nucleocytoplasmic transport: the soluble phase. Annu Rev Biochem 67, 265-306.

Memisoglu, A., and Samson, L. (2000). Base excision repair in yeast and mammals. Mutat Res 451, 39-51.

Miao, F., Bouziane, M., Dammann, R., Masutani, C., Hanaoka, F., Pfeifer, G. P., and O'Connor, T. R. (2000). 3-methyladenine-DNA glycosylase (MPG protein) interacts with human RAD23 proteins. J Biol Chem 275, 28433-28438.

Mowen, K., and David, M. (2000). Regulation of STAT1 nuclear export by Jak1. Mol Cell Biol 20, 7273-7281.

Ng, J. M. Y., Vrieling, H., Sugasawa, K., Ooms, M. P., Grootegoed, J. A., Vreeburg, J. T., Visser, P., Beems, R. B., Gorgels, T. G., Hanaoka, F., et al. (2002). Developmental defects and male sterility in mice lacking the ubiquitin-like DNA repair gene mHR23B. Mol Cell Biol 22, 1233-1245.

Nigg, E. A. (1997). Nucleocytoplasmic transport: signals, mechanisms and regulation. Nature 386, 779-787.

Ortolan, T. G., Tongaonkar, P., Lambertson, D., Chen, L., Schauber, C., and Madura, K. (2000). The DNA repair protein Rad23 is a negative regulator of multi-ubiquitin chain assembly. Nat Cell Biol 2, 601-608.

Rao, H., and Sastry, A. (2002). Recognition of specific ubiquitin conjugates is important for the proteolytic functions of the UBA domain proteins Dsk2 and Rad23. J Biol Chem 22.

Roth, J., Dobbelstein, M., Freedman, D. A., Shenk, T., and Levine, A. J. (1998). Nucleo-cytoplasmic shuttling of the hdm2 oncoprotein regulates the levels of the p53 protein via a pathway used by the human immunodeficiency virus rev protein. Embo J 17, 554-564.

Russell, S. J., Reed, S. H., Huang, W., Friedberg, E. C., and Johnston, S. A. (1999). The 19S regulatory complex of the proteasome functions independently of proteolysis in nucleotide excision repair. Mol Cell 3, 687-695.

Schauber, C., Chen, L., Tongaonkar, P., Vega, I., Lambertson, D., Potts, W., and Madura, K. (1998). Rad23 links DNA repair to the ubiquitin/proteasome pathway. Nature 391, 715-718.

Siede, W., and Eckardt-Schupp, F. (1986). DNA repair genes of Saccharomyces cerevisiae: complementing rad4 and rev2 mutations by plasmids which cannot be propagated in Escherichia coli. Curr Genet 11, 205-210.

Sionov, R. V., Coen, S., Goldberg, Z., Berger, M., Bercovich, B., Ben-Neriah, Y., Ciechanover, A., and Haupt, Y. (2001). c-Abl regulates p53 levels under normal and stress conditions by preventing its nuclear export and ubiquitination. Mol Cell Biol 21, 5869-5878.

Sugasawa, K., Okamoto, T., Shimizu, Y., Masutani, C., Iwai, S., and Hanaoka, F. (2001). A multistep damage recognition mechanism for global genomic nucleotide excision repair. Genes Dev 15, 507-521.

Sugasawa, K., Ng, J. M. Y., Masutani, C., Iwai, S., van der Spek, P. J., Eker, A. P., Hanaoka, F., Bootsma, D., and Hoeijmakers, J. H. J. (1998). Xeroderma pigmentosum group C protein complex is the initiator of global genome nucleotide excision repair. Mol Cell 2, 223-232.

Sugasawa, K., Ng, J. M. Y., Masutani, C., Maekawa, T., Uchida, A., van der Spek, P. J., Eker, A. P., Rademakers, S., Visser, C., Aboussekhra, A., et al. (1997). Two human homologs of Rad23 are functionally interchangeable in complex formation and stimulation of XPC repair activity. Mol Cell Biol 17, 6924-6931.

Sugasawa, K., Masutani, C., Uchida, A., Maekawa, T., van der Spek, P. J., Bootsma, D., Hoeijmakers, J. H. J., and Hanaoka, F. (1996). HHR23B, a human Rad23 homolog, stimulates XPC protein in nucleotide excision repair in vitro. Mol Cell Biol 16, 4852-4861.

Sutton, M. D., Smith, B. T., Godoy, V. G., and Walker, G. C. (2000). The SOS response: recent insights into umuDC-dependent mutagenesis and DNA damage tolerance. Annu Rev Genet 34, 479-497.

Uchida, A., Sugasawa, K., Masutani, C., Dohmae, N., Araki, M., Yokoi, M., Ohkuma, Y., and Hanaoka, F. (2002). The carboxy-terminal domain of the XPC protein plays a crucial role in nucleotide excision repair through interactions with transcription factor IIH. DNA Repair 1, 449-461.

van der Spek, P. J., Eker, A., Rademakers, S., Visser, C., Sugasawa, K., Masutani, C., Hanaoka, F., Bootsma, D., and Hoeijmakers, J. H. J. (1996a). XPC and human homologs of RAD23: intracellular localization and relationship to other nucleotide excision repair complexes. Nucleic Acids Res 24, 2551-2559.

van der Spek, P. J., Visser, C. E., Hanaoka, F., Smit, B., Hagemeijer, A., Bootsma, D., and Hoeijmakers, J. H. J. (1996b). Cloning, comparative mapping, and RNA expression of the mouse homologues of the *Saccharomyces cerevisiae* nucleotide excision repair gene RAD23. Genomics 31, 20-27.

Venema, J., van Hoffen, A., Natarajan, A. T., van Zeeland, A. A., and Mullenders, L. H. (1990). The residual repair capacity of xeroderma pigmentosum complementation group C fibroblasts is highly specific for transcriptionally active DNA. Nucleic Acids Res 18, 443-448.

Verhage, R. A., Zeeman, A. M., Lombaerts, M., van de Putte, P., and Brouwer, J. (1996). Analysis of gene- and strand-specific repair in the moderately UV-sensitive *Saccharomyces cerevisiae* rad23 mutant. Mutat Res 362, 155-165.

Vermeulen, W., Scott, R. J., Rodgers, S., Muller, H. J., Cole, J., Arlett, C. F., Kleijer, W. J., Bootsma, D., Hoeijmakers, J. H. J., and Weeda, G. (1994). Clinical heterogeneity within xeroderma pigmentosum associated with mutations in the DNA repair and transcription gene ERCC3. Am J Hum Genet 54, 191-200.

Volker, M., Moné, M. J., Karmakar, P., Hoffen, A., Schul, W., Vermeulen, W., Hoeijmakers, J. H. J., van Driel, R., Zeeland, A. A., and Mullenders, L. H. F. (2001). Sequential assembly of the nucleotide excision repair factors in vivo. Mol Cell 8, 213-224.

Watkins, J. F., Sung, P., Prakash, L., and Prakash, S. (1993). The *Saccharomyces cerevisiae* DNA repair gene RAD23 encodes a nuclear protein containing a ubiquitin-like domain required for biological function. Mol Cell Biol 13, 7757-7765.

Wei, S., and Friedberg, E. C. (1998). A fragment of the yeast DNA repair protein Rad4 confers toxicity to *E. coli* and is required for its interaction with Rad7 protein. Mutat Res 400, 127-133.

Wiertz, E. J., Jones, T. R., Sun, L., Bogyo, M., Geuze, H. J., and Ploegh, H. L. (1996). The human cytomegalovirus US11 gene product dislocates MHC class I heavy chains from the endoplasmic reticulum to the cytosol. Cell 84, 769-779.

Wilkinson, C. R., Seeger, M., Hartmann-Petersen, R., Stone, M., Wallace, M., Semple, C., and Gordon, C. (2001). Proteins containing the UBA domain are able to bind to multi-ubiquitin chains. Nat Cell Biol 3, 939-943.

Wood, R. D., Hanawalt, P. C., Mer, G., and Cooper, P. K. (2001a). Nucleotide excision repair. In Biological responses to DNA damage. Cold Spring Harb Symp Quant Biol LXV.

Wood, R. D., Mitchell, M., Sgouros, J., and Lindahl, T. (2001b). Human DNA repair genes. Science 291, 1284-1289.

Yagita, K., Tamanini, F., Yasuda, M., Hoeijmakers, J. H., van der Horst, G. T., and Okamura, H. (2002). Nucleocytoplasmic shuttling and mCRY-dependent inhibition of ubiquitylation of the mPER2 clock protein. Embo J 21, 1301-1314.

Yokoi, M., Masutani, C., Maekawa, T., Sugasawa, K., Ohkuma, Y., and Hanaoka, F. (2000). The xeroderma pigmentosum group C protein complex XPC-HR23B plays an important role in the recruitment of transcription factor IIH to damaged DNA. J Biol Chem 275, 9870-9875.

Zhu, Q., Wani, G., Wani, M. A., and Wani, A. A. (2001). Human homologue of yeast Rad23 protein A interacts with p300/cyclic AMP-responsive element binding (CREB)-binding protein to down-regulate transcriptional activity of p53. Cancer Res 61, 64-70.

---

What is claimed is:

1. A method for detecting a DNA lesion that is a substrate for global genome nucleotide excision repair in a mouse embryonic fibroblast that is deficient in endogenous HR23A and HR23B and that comprises an exogenous nucleic acid expressing HR23 protein or a functional part thereof, the method comprising:
   determining if there is an overall intranuclear accumulation of full-length xeroderma pigmentosum group C (XPC) protein within the mouse embryonic fibroblast; and
   correlating said overall intranuclear accumulation of full-length xeroderma pigmentosum group C protein with a DNA lesion that is a substrate for global genome nucleotide excision repair in the mouse embryonic fibroblast.

2. The method according to claim 1, wherein said mouse embryonic fibroblast is overexpressing HR23A and/or HR23B protein, or a functional part thereof.

3. The method according to claim 1, wherein said mouse embryonic fibroblast is part of a cell line.

4. The method according to claim 1, wherein said mouse embryonic fibroblast is provided with a nucleic acid encoding human HR23A protein or a functional part thereof.

5. The method according to claim 1, wherein said mouse embryonic fibroblast is provided with a nucleic acid encoding murine HR23A protein or a functional part thereof.

6. The method according to claim 1, wherein said mouse embryonic fibroblast has been provided with a nucleic acid encoding human HR23B protein or a functional part thereof.

7. The method according to claim 1, wherein said mouse embryonic fibroblast is provided with a nucleic acid encoding murine HR23B protein or a functional part thereof.

8. The method according to claim 1, wherein said xeroderma pigmentosum group C protein comprises a human xeroderma pigmentosum group C protein.

9. The method according to claim 1, wherein the XPC protein comprises a label.

10. A method for determining whether an agent is capable of inducing a DNA lesion that is a substrate for global genome nucleotide excision repair or capable of at least in part inhibiting a cellular process, the cellular process resulting in accumulation of xeroderma pigmentosum group C protein in a mouse embryonic fibroblast that is deficient in endogenous HR23A and HR23B and that comprises an exogenous nucleic acid expressing an HR23 protein or a functional part thereof, the method comprising:
    exposing at least one mouse embryonic fibroblast that is deficient in endogenous HR23A and HR23B and that comprises an exogenous nucleic acid expressing an HR23 protein or a functional part thereof to the agent;
    determining if there is an overall intranuclear accumulation of full-length xeroderma pigmentosum group C (XPC) protein within the mouse embryonic fibroblast; and
    correlating the overall intranuclear accumulation of full-length xeroderma pigmentosum group C protein with said agent's ability to induce a DNA lesion that is a substrate for global genome nucleotide excision repair or to at least in part inhibit a cellular process in the mouse embryonic fibroblast; wherein the cellular process is selected from the group consisting of proteasomal proteolysis, nucleo-cytoplasm shuttling, and any combination thereof.

11. The method according to claim 10, wherein the XPC protein comprises a label.

12. The method according to any one of claims 9 or 11, wherein said label comprises green fluorescent protein or luciferase.

\* \* \* \* \*

UNITED STATES PATENT AND TRADEMARK OFFICE
CERTIFICATE OF CORRECTION

PATENT NO. : 7,820,374 B2  Page 1 of 1
APPLICATION NO. : 10/301498
DATED : October 26, 2010
INVENTOR(S) : Jan H. J. Hoeijmakers et al.

It is certified that error appears in the above-identified patent and that said Letters Patent is hereby corrected as shown below:

On the title page:
In ITEM (75) Inventors: change "Mei Yin Ng, Philadelphia, PA (US)" to
--Mei Yin Ng, Den Haag (NL)--

In ITEM (73) Assignee: change "Rotterdan (NL)" to --Rotterdam (NL)--

In the specification:
COLUMN 5, LINE 47, change "hXCPC-GFP/hHr23B." to --hXPC-GFP/hHr23B.--

In the claims:
CLAIM 1, COLUMN 37, LINE 6, change "expressing HR23" to --expressing an HR23--

Signed and Sealed this
Thirtieth Day of August, 2011

David J. Kappos
*Director of the United States Patent and Trademark Office*

SEQUENCE LISTING

```
<160> NUMBER OF SEQ ID NOS: 21

<210> SEQ ID NO 1
<211> LENGTH: 21
<212> TYPE: DNA
<213> ORGANISM: Artificial
<220> FEATURE:
<223> OTHER INFORMATION: primer mHR23Ap1

<400> SEQUENCE: 1
atgggacttg ggcataggtg a                                          21

<210> SEQ ID NO 2
<211> LENGTH: 20
<212> TYPE: DNA
<213> ORGANISM: Artificial
<220> FEATURE:
<223> OTHER INFORMATION: primer mHR23Ap2
```

<400> SEQUENCE: 2
tcttcagcca ggcctcttac                                                                  20

<210> SEQ ID NO 3
<211> LENGTH: 25
<212> TYPE: DNA
<213> ORGANISM: artificial
<220> FEATURE:
<223> OTHER INFORMATION: primer anti-sense neo

<400> SEQUENCE: 3
atctgcgtgt tcgaattcgc caatg                                                            25

<210> SEQ ID NO 4
<211> LENGTH: 21
<212> TYPE: DNA
<213> ORGANISM: Artificial
<220> FEATURE:
<223> OTHER INFORMATION: primer mHR23Bp1

<400> SEQUENCE: 4
gtaaaggcat tgaaagagaa g                                                                21

<210> SEQ ID NO 5
<211> LENGTH: 21
<212> TYPE: DNA
<213> ORGANISM: Artificial
<220> FEATURE:
<223> OTHER INFORMATION: primer mHR23Bp2

<400> SEQUENCE: 5
ctacagtctt gtttctgaca g                                                                21

<210> SEQ ID NO 6
<211> LENGTH: 20
<212> TYPE: DNA
<213> ORGANISM: Artificial
<220> FEATURE:
<223> OTHER INFORMATION: primer anti-sense pgk3

<400> SEQUENCE: 6 tagggagga gtagaaggtg                                                                   20

<210> SEQ ID NO 7
<211> LENGTH: 12
<212> TYPE: PRT
<213> ORGANISM: Artificial
<220> FEATURE:
<223> OTHER INFORMATION: Consensus sequence NES
<220> FEATURE:
<221> NAME/KEY: MISC_FEATURE
<222> LOCATION: (2)..(2)
<223> OTHER INFORMATION: Can be any amino acid
<220> FEATURE:
<221> NAME/KEY: MISC_FEATURE
<222> LOCATION: (3)..(4)
<223> OTHER INFORMATION: Can be any amino acid or absent
<220> FEATURE:
<221> NAME/KEY: MISC_FEATURE
<222> LOCATION: (6)..(7)
<223> OTHER INFORMATION: Can be any amino acid
<220> FEATURE:
<221> NAME/KEY: MISC_FEATURE
<222> LOCATION: (8)..(9)
<223> OTHER INFORMATION: Can be any amino acid or absent
<220> FEATURE:
<221> NAME/KEY: MISC_FEATURE
<222> LOCATION: (11)..(11)
<223> OTHER INFORMATION: Can be any amino acid

```
<400> SEQUENCE: 7

Leu Xaa Xaa Xaa Leu Xaa Xaa Xaa Xaa Leu Xaa Leu
1               5                   10

<210> SEQ ID NO 8
<211> LENGTH: 11
<212> TYPE: PRT
<213> ORGANISM: Artificial
<220> FEATURE:
<223> OTHER INFORMATION: human XPC NES-like domain 1

<400> SEQUENCE: 8

Leu Leu Pro Val Lys Pro Val Glu Ile Glu Ile
1               5                   10

<210> SEQ ID NO 9
<211> LENGTH: 11
<212> TYPE: PRT
<213> ORGANISM: artificial
<220> FEATURE:
<223> OTHER INFORMATION: mouse XPC NES-like domain 1

<400> SEQUENCE: 9

Asp Met Pro Val Lys Ala Val Glu Ile Glu Ile
1               5                   10

<210> SEQ ID NO 10
<211> LENGTH: 27
<212> TYPE: PRT
<213> ORGANISM: Artificial
<220> FEATURE:
<223> OTHER INFORMATION: mouse and human XPC NES-like domain 2
<220> FEATURE:
<221> NAME/KEY: MISC_FEATURE
<222> LOCATION: (1)..(9)
<223> OTHER INFORMATION: leucine rich region
<220> FEATURE:
<221> NAME/KEY: MISC_FEATURE
<222> LOCATION: (6)..(14)
<223> OTHER INFORMATION: leucine rich region
<220> FEATURE:
<221> NAME/KEY: MISC_FEATURE
<222> LOCATION: (12)..(22)
<223> OTHER INFORMATION: leucine rich region
<220> FEATURE:
<221> NAME/KEY: MISC_FEATURE
<222> LOCATION: (20)..(27)
<223> OTHER INFORMATION: leucine rich region

<400> SEQUENCE: 10

Leu Val His Ile Phe Leu Leu Ile Leu Arg Ala Leu Gln Leu Leu Thr
1               5                   10                  15

Arg Leu Val Leu Ser Leu Gln Pro Ile Pro Leu
            20                  25

<210> SEQ ID NO 11
<211> LENGTH: 30
<212> TYPE: PRT
<213> ORGANISM: Artificial
<220> FEATURE:
<223> OTHER INFORMATION: human XPC NES-like domain 3
<220> FEATURE:
<221> NAME/KEY: MISC_FEATURE
<222> LOCATION: (8)..(16)
<223> OTHER INFORMATION: leucine rich domain

<400> SEQUENCE: 11

Val Tyr Leu Phe Leu Pro Ser Met Met Pro Ile Gly Cys Val Gln Leu
```

```
                    1               5                  10                 15
Asn Leu Pro Asn Leu His Arg Val Ala Arg Lys Leu Asp Ile
            20                  25                 30

<210> SEQ ID NO 12
<211> LENGTH: 30
<212> TYPE: PRT
<213> ORGANISM: Artificial
<220> FEATURE:
<223> OTHER INFORMATION: mouse XPC NES-like domain 3
<220> FEATURE:
<221> NAME/KEY: MISC_FEATURE
<222> LOCATION: (1)..(11)
<223> OTHER INFORMATION: leucine rich domain
<220> FEATURE:
<221> NAME/KEY: MISC_FEATURE
<222> LOCATION: (21)..(30)
<223> OTHER INFORMATION: leucine rich domain

<400> SEQUENCE: 12

Val Tyr Leu Phe Leu Pro Ser Met Met Pro Val Gly Cys Val Gln Met
1               5                   10                  15

Thr Leu Pro Asn Leu Asn Arg Val Ala Arg Lys Leu Gly Ile
            20                  25                  30

<210> SEQ ID NO 13
<211> LENGTH: 27
<212> TYPE: PRT
<213> ORGANISM: Artificial
<220> FEATURE:
<223> OTHER INFORMATION: mouse mXPC NES-like domain 2

<400> SEQUENCE: 13

Leu Val His Ile Phe Leu Leu Ile Leu Arg Ala Leu Gln Leu Leu Thr
1               5                   10                  15

Arg Leu Val Leu Ser Leu Gln Pro Ile Pro Leu
            20                  25

<210> SEQ ID NO 14
<211> LENGTH: 9
<212> TYPE: PRT
<213> ORGANISM: Artificial
<220> FEATURE:
<223> OTHER INFORMATION: mouse mXPC/hXPC NES-like domain 2 conserved
      region

<400> SEQUENCE: 14

Leu Leu Ile Leu Arg Ala Leu Gln Leu
1               5

<210> SEQ ID NO 15
<211> LENGTH: 8
<212> TYPE: PRT
<213> ORGANISM: Artificial
<220> FEATURE:
<223> OTHER INFORMATION: mouse mXPC/hXPC NES-like domain 2 conserved
      region

<400> SEQUENCE: 15

Leu Ser Leu Gln Pro Ile Pro Leu
1               5

<210> SEQ ID NO 16
<211> LENGTH: 9
<212> TYPE: PRT
<213> ORGANISM: Artificial
<220> FEATURE:
```

```
<223> OTHER INFORMATION: mouse mXPC/hXPC NES-like domain 2 conserved
      region

<400> SEQUENCE: 16

Leu Val His Ile Phe Leu Leu Ile Leu
1               5

<210> SEQ ID NO 17
<211> LENGTH: 11
<212> TYPE: PRT
<213> ORGANISM: Artificial
<220> FEATURE:
<223> OTHER INFORMATION: mouse mXPC/hXPC NES-like domain 2 conserved
      region

<400> SEQUENCE: 17

Leu Gln Leu Leu Thr Arg Leu Val Leu Ser Leu
1               5                   10

<210> SEQ ID NO 18
<211> LENGTH: 9
<212> TYPE: PRT
<213> ORGANISM: Artificial
<220> FEATURE:
<223> OTHER INFORMATION: mouse mXPC/hXPC NES-like domain 3 conserved
      region

<400> SEQUENCE: 18

Met Met Pro Ile Gly Cys Val Gln Leu
1               5

<210> SEQ ID NO 19
<211> LENGTH: 11
<212> TYPE: PRT
<213> ORGANISM: Artificial
<220> FEATURE:
<223> OTHER INFORMATION: mouse mXPC/hXPC NES-like domain 3 conserved
      region

<400> SEQUENCE: 19

Val Tyr Leu Phe Leu Pro Ser Met Met Pro Val
1               5                   10

<210> SEQ ID NO 20
<211> LENGTH: 10
<212> TYPE: PRT
<213> ORGANISM: Artificial
<220> FEATURE:
<223> OTHER INFORMATION: mouse mXPC/hXPC NES-like domain 3 conserved
      region

<400> SEQUENCE: 20

Leu Asn Arg Val Ala Arg Lys Leu Gly Ile
1               5                   10

<210> SEQ ID NO 21
<211> LENGTH: 6
<212> TYPE: PRT
<213> ORGANISM: Artificial
<220> FEATURE:
<223> OTHER INFORMATION: His6 tag antibody

<400> SEQUENCE: 21

His His His His His His
1               5
```